(12) United States Patent
Voss

(10) Patent No.: US 10,808,276 B2
(45) Date of Patent: *Oct. 20, 2020

(54) METHOD FOR ISOLATING NUCLEIC ACIDS

(71) Applicant: QIAGEN GmbH, Hilden (DE)

(72) Inventor: Thorsten Voss, Hilden (DE)

(73) Assignee: QIAGEN GmbH, Hilden (DE)

( * ) Notice: Subject to any disclaimer, the term of this patent is extended or adjusted under 35 U.S.C. 154(b) by 255 days.

This patent is subject to a terminal disclaimer.

(21) Appl. No.: 15/596,275

(22) Filed: May 16, 2017

(65) Prior Publication Data
US 2018/0094296 A1 Apr. 5, 2018

Related U.S. Application Data

(63) Continuation of application No. 14/238,625, filed as application No. PCT/EP2012/065819 on Aug. 13, 2012, now Pat. No. 9,695,465.

(30) Foreign Application Priority Data

Aug. 12, 2011 (EP) .................................. 11177426

(51) Int. Cl.
C12Q 1/6806 (2018.01)
C12N 15/10 (2006.01)

(52) U.S. Cl.
CPC ....... C12Q 1/6806 (2013.01); C12N 15/1003 (2013.01)

(58) Field of Classification Search
CPC ........ G01H 1/34; C12N 15/1003; C12Q 1/68; C07H 21/00
See application file for complete search history.

(56) References Cited

U.S. PATENT DOCUMENTS

| | | | |
|---|---|---|---|
| 5,010,183 A * | 4/1991 | Macfarlane ........ | C12N 15/1003 435/262 |
| 5,234,809 A * | 8/1993 | Boom .................... | C07H 21/00 422/504 |
| 5,346,994 A | 9/1994 | Chomczynski | |
| 5,457,025 A * | 10/1995 | Collins ................ | C12Q 1/6832 435/6.14 |
| 5,728,822 A * | 3/1998 | Macfarlane ........... | C07C 211/62 536/25.41 |
| 5,906,744 A | 5/1999 | Carroll et al. | |
| 5,985,572 A | 11/1999 | Macfarlane | |
| 6,180,778 B1 * | 1/2001 | Bastian .............. | C12N 15/1006 536/25.3 |
| 6,270,970 B1 * | 8/2001 | Smith ..................... | B01J 41/20 435/6.16 |
| 6,602,718 B1 * | 8/2003 | Augello ............... | C12Q 1/6806 252/408.1 |
| 6,776,959 B1 | 8/2004 | Helftenbein | |
| 7,270,953 B2 | 9/2007 | Holländer et al. | |
| 7,683,035 B1 * | 3/2010 | Erbacher ............ | C12N 15/1003 424/450 |
| 7,838,233 B2 * | 11/2010 | Korfhage ........... | C12N 15/1003 435/6.1 |
| 8,008,475 B1 | 8/2011 | Bastian et al. | |
| 8,865,405 B2 | 10/2014 | Bost et al. | |
| 9,695,465 B2 * | 7/2017 | Voss ...................... | C12Q 1/6806 |
| 9,896,682 B2 * | 2/2018 | Gong ................. | C12N 15/1003 |
| 2001/0006697 A1 | 7/2001 | Elkin et al. | |
| 2001/0041332 A1 * | 11/2001 | Hillebrand ......... | C12N 15/1006 435/6.16 |
| 2003/0073830 A1 * | 4/2003 | Heath ................ | C12N 15/1006 536/25.4 |
| 2003/0096772 A1 * | 5/2003 | Crooke .............. | C12N 15/1137 514/44 A |

(Continued)

FOREIGN PATENT DOCUMENTS

| | | |
|---|---|---|
| EP | 0 343 934 A2 | 11/1989 |
| EP | 1 000 734 A2 | 5/2000 |

(Continued)

OTHER PUBLICATIONS

Material Safty Data Sheet for ALBuffer produced by Qiagen GmbH downloaded from the internet on May 10, 2019 (Year: 2013).*
De Vries et al., Evaluation of DNA extraction methods for dried blood spots in the diagnosis of congenital cytomegalovirus infection. J. of Clinical Virology 46S :S37-S42 (Year: 2009).*
Flieger J., Effect of mobile phase composition on the retention of selected alkaloids in reversed-phase liquid chromatography with chaotropic salts. J. of Chromatography A 1175: 207-216 (Year: 2007).*

(Continued)

Primary Examiner — Ethan C Whisenant
(74) Attorney, Agent, or Firm — Seed IP Law Group LLP

(57) ABSTRACT

The present invention pertains to a method for isolating nucleic acids from a sample, preferably a blood sample, comprising the following steps:
a) obtaining a sample which has been stabilised by the use of at least one cationic detergent, wherein the cationic detergent has formed complexes with the nucleic acids;
b) obtaining the complexes optionally together with other sample components from the stabilised sample, wherein said complexes comprise the nucleic acids to be isolated;
c) resuspending the complexes and optionally adding one or more additives before, during and/or after resuspension, thereby obtaining a resuspended sample comprising at least
  i) the nucleic acid to be isolated;
  ii) at least one chaotropic agent; and
  iii) at least one chelating agent;
and
d) isolating nucleic acids from the resuspended sample.
It was found that adding a chelating agent during resuspension considerably increases the nucleic acid yield as the formation of precipitates which irreversibly adhere to the container wall is considerably reduced.

32 Claims, 5 Drawing Sheets

(56) References Cited

U.S. PATENT DOCUMENTS

| | | |
|---|---|---|
| 2003/0165943 A1 | 9/2003 | Oelmuller et al. |
| 2004/0014070 A1* | 1/2004 | Pinsl-Ober ......... C12N 15/1006 435/5 |
| 2005/0153292 A1 | 7/2005 | Stordeur et al. |
| 2005/0191760 A1 | 9/2005 | Heath et al. |
| 2006/0141488 A1* | 6/2006 | Huang ................... C07H 21/02 435/5 |
| 2006/0159916 A1 | 7/2006 | Dubrow et al. |
| 2008/0132694 A1* | 6/2008 | Himmelreich ..... C12N 15/1013 536/25.41 |
| 2009/0181378 A1* | 7/2009 | Sanders ............... C12Q 1/6886 435/6.11 |
| 2009/0280470 A1* | 11/2009 | Fare ................... C12N 15/1017 435/2 |
| 2009/0286314 A1* | 11/2009 | Israelsson ............... C07K 14/46 435/348 |
| 2010/0099149 A1 | 4/2010 | Birnboim et al. |
| 2010/0285578 A1 | 11/2010 | Selden et al. |
| 2011/0111409 A1* | 5/2011 | Sinicropi ........... C12N 15/1003 435/6.11 |
| 2012/0141497 A1* | 6/2012 | Gallo ....................... C07K 1/18 424/158.1 |
| 2012/0149587 A1* | 6/2012 | Landers ........... G01N 33/54326 506/7 |
| 2012/0196755 A1 | 8/2012 | Brewer et al. |
| 2013/0164819 A1 | 6/2013 | Sjöblom et al. |
| 2015/0252354 A1 | 9/2015 | Lai et al. |
| 2016/0108463 A1 | 4/2016 | Fischer et al. |

FOREIGN PATENT DOCUMENTS

| | | |
|---|---|---|
| EP | 1 031 626 A1 | 8/2000 |
| EP | 1 260 595 A2 | 11/2002 |
| EP | 0 880 537 B1 | 12/2004 |
| EP | 1 873 243 A1 | 1/2008 |
| EP | 1 000 043 B1 | 10/2009 |
| EP | 2 345 719 A1 | 7/2011 |
| WO | 95/21849 A1 | 8/1995 |
| WO | 96/41811 A1 | 12/1996 |
| WO | 98/31461 A1 | 7/1998 |
| WO | 98/31840 A1 | 7/1998 |
| WO | 01/71732 A2 | 9/2001 |
| WO | 02/00599 A1 | 1/2002 |
| WO | 03/004150 A1 | 1/2003 |
| WO | 2004/003231 A2 | 1/2004 |
| WO | 2004/013155 A2 | 2/2004 |
| WO | 2007/049326 A1 | 5/2007 |
| WO | 2007/080178 A2 | 7/2007 |

OTHER PUBLICATIONS

Francesca et al., Performance evaluation of the automated NucliSens easyMAG nucleic acid extraction platform in comparison with QIAamp Mini kit from clinical specimens. Diagnostic Microbiology and Infectious Disease. 64 :158-165 (Year: 2009).*

Huang et al., Optimization of DNase I Removal of Contaminating DNA from RNA for Use in Quantitative RNA-PCR. Biotechniques 20(6) : 1014 (Year: 1996).*

Loens et al., Evaluation of NucliSens easyMAG for Automated Nucleic Acid Extraction from Various Clinical Specimens. J. of Clinical Microbiology 45(2) :421-425 (Year: 2007).*

Moelbert et al., Kosmotropes and chaotropes: modelling preferential exclusion, binding and aggregate stability. Biophysical Chemistry 112 : 45-47 (Year: 2004).*

Tetradecyltrimethylammonium oxalate (Structure) Wikipedia Entry. (Year: 2020).*

Chomczynski et al., "The single-step method of RNA isolation by acid guanidinium thiocyanate-phenol-chloroform extraction: twenty-something years on," *Nature Protocols* 1(2):581-585 (2006).

Genov et al., "Stability of subtilisins and related proteinases (subtilases)," *Int. J. Peptide Protein Res.* 45:391-400 (1995).

Hartman et al., "The dependence of the rate of RNase A catalyzed hydrolysis of ribosomes and rRNA on the concentration of magnesium and ammonium ions," *Biochemical and Biophysical Research Communications* 45(5):1307-1311, 2 pages, (abstract only), (Dec. 3, 1971).

Yang et al., "Inactivation during denaturation of ribonuclease A guanidinium chloride is accompanied by unfolding at the active site," *Biochem J.* 305:379-384 (1995).

* cited by examiner

METHOD FOR ISOLATING NUCLEIC ACIDS

CROSS REFERENCE TO RELATED APPLICATIONS

The present application is a continuation application of U.S. application Ser. No. 14/238,625 filed Feb. 12, 2014, now pending, which is a U.S. national phase application of PCT/EP2012/065819 filed Aug. 13, 2012, which claims priority to EP Application No. 11177426.1 filed Aug. 12, 2011. U.S. application Ser. No. 14/238,625 is herein incorporated by reference in its entity.

The work leading to this invention has received funding from the European Community's Seventh Framework Programme (FP7/2007-2013) under grant agreement n° 222916.

FIELD OF THE INVENTION

The present invention pertains to the field of isolating nucleic acids, in particular the isolation of RNA, from biological samples, in particular from a blood sample, with high yield and integrity.

BACKGROUND OF THE INVENTION

Several methods for isolating nucleic acids such as RNA and/or DNA are known in the prior art that are based on different principles. Examples of common nucleic acid isolation methods include but are not limited to extraction, solid-phase extraction, phenol-chloroform extraction, chromatography, precipitation and combinations thereof. Very common are nucleic acid isolation methods which involve the use of chaotropic agents and/or alcohol in order to bind the nucleic acids to a solid phase, e.g. a solid phase comprising or consisting of silica. The isolation of RNA is particularly challenging, because RNAses are omnipresent in rather high amounts and are active over a broad temperature range and usually do not need co-factors for their activity. Therefore, it is a challenge to provide a RNA isolation method which provides the RNA with good yield and quality.

Furthermore, in many fields such as e.g. the diagnostic field it is desirous or even mandatory to isolate the nucleic acids from a large number of samples. For this purpose it is common to use automated processes (wherein e.g. many samples are processed at the same time). To assist the user and to reduce hands-on-time, robotic systems are commonly used that can process a large number of samples in parallel. Usually, the samples are prepared manually for nucleic acid isolation and are then entered into the robotic system. Respective manual preparation steps are e.g. common for stabilised blood samples. Respective manual steps include e.g. the centrifugation of the stabilised sample to generate a nucleic acid containing pellet and the resuspension of the pellet e.g. in a resuspension buffer (thereby reducing the sample volume). The respectively resuspended samples are then ready e.g. for sample digestion and isolation and are placed into the robotic system. Examples of commercially available robotic systems that operate according to this or a similar principle include but are not limited to QIAsymphony (QIAGEN), QIAcube (QIAGEN) and MagnaPure 96 (ROCHE).

Even though these robotic systems provide remarkable advantages when processing a large number of samples, they also have certain limitations. E.g. said robotic systems can usually only process a certain number of samples at one time. Said number is often lower than the number of samples that is manually prepared as one batch for nucleic acid isolation. Thus, not all of the prepared samples can be processed at the same time. This has the effect that the samples prepared for nucleic acid isolation often have different holding times between their preparation for nucleic acid isolation (e.g. the centrifugation and resuspension of the pellet as described above) and the actual nucleic acid isolation. While the first batch of the prepared samples is processed in the robotic system, the other prepared samples are put on hold. It was found that variations in the holding time of the prepared sample can influence the quality of the isolated nucleic acid as well as the nucleic acid yield. During longer holding times, a portion of the nucleic acids can form precipitates which irreversible stick to the container and thus, can not be purified. Furthermore, the integrity of the nucleic acids, in particular of RNA, can be corrupted. Thus, the nucleic acid quantity and/or quality of the second and subsequent batch of the prepared samples that are processed in the robotic systems are often lower. Hence, a longer holding time may reduce the quality and/or the quantity of the isolated nucleic acids. This in particular poses a problem if complex samples are processed, such as e.g. blood or samples derived from blood and/or samples that were stabilised using a specific chemistry. This problem is further aggravated if large sample volumes (e.g. 1.5 ml and more) are processed. This loss in yield and/or integrity can pose problems in particular in sensitive application fields such as e.g. the diagnostic field wherein an uniform nucleic acid isolation with respect to yield and quantity is important and hence, variations due to the used nucleic acid isolation method must be avoided.

Furthermore, methods that use magnetic beads as solid phase for binding and isolating the nucleic acids often show a reduced nucleic acid yield compared to comparable methods that use a nucleic acid binding membrane instead. Therefore, a loss in nucleic acid yield due to the precipitate formation has an even stronger impact on respective methods and system that use magnetic particles as nucleic acid binding solid phase.

Hence, there is a need in the state of the art to provide a nucleic acid isolation protocol which provides comparable high nucleic acid yields and also a high yield of small nucleic acids, even if the holding times vary between samples and also during extended holding times, a high nucleic acid, in particular RNA integrity.

Therefore, it is an object of the present invention to provide an improved method for isolating a nucleic acid, in particular RNA, from a sample, in particular a blood sample. Furthermore, it is the object of the present invention to provide a method that allows the isolation of nucleic acids from a plurality of samples with a comparable quality and/or quantity, even if the holding times between the preparation of the samples for isolation and the actual isolation of the nucleic acids varies.

SUMMARY OF THE INVENTION

The present invention is based on the surprising finding that variations in the nucleic acid yield and quality can be significantly reduced if at least one chaotropic agent and at least one chelating agent are included in the sample that is prepared for nucleic acid isolation. It was found that including at least one chaotropic agent and at least one chelating agent into the sample prepared for nucleic acid isolation has the advantage that the quality and yield of the nucleic acids that are isolated from respectively prepared samples is substantially maintained even if the prepared samples stand for a prolonged period of time (e.g. selected from 0.5 h to 12 h, 0.75 h to 11 h, 1 h to 10 h, 1.25 h to 9 h, 1.5 h to 8.5 h, 1.75 h to 8 h, 1.75 h to 7.5 h, 1.25 h to 7 hours, 1.5 h to 6.5 h, 1.75 h to 6 h, 2 h to 5.5 h) before the nucleic acids are actually isolated from the respectively prepared samples. This advantage is particularly important when processing a large number of samples because in this case variations in the holding time between samples are rather common, in particular when using an automated system. However, this advantage is also generally important as it reduces the need to directly isolate the nucleic acids from the samples that are prepared for nucleic acid isolation. This provides more flexibility.

According to a first aspect, the present invention provides a method for isolating nucleic acids, preferably RNA, from a sample, preferably a blood sample, comprising the following steps:
 a) obtaining a sample which has been stabilised by the use of at least one cationic detergent, wherein the cationic detergent has formed complexes with the nucleic acids;
 b) obtaining the complexes optionally together with other sample components from the stabilised sample, wherein said complexes comprise the nucleic acids to be isolated;
 c) resuspending the complexes and optionally adding one or more additives before, during and/or after resuspension, thereby obtaining a resuspended sample comprising at least
  i) the nucleic acids to be isolated;
  ii) at least one chaotropic agent; and
  iii) at least one chelating agent;
 and
 d) isolating nucleic acids from the resuspended sample.

As discussed above, the method according to the present invention allows to isolate nucleic acids with comparable good yield and quality from samples, even if the holding time between step c) and step d) should vary. The addition of the chaotropic agent preserves the quality of the nucleic acids contained in the resuspended sample, in particular of RNA. However, adding a chaotropic agent has the drawback that the nucleic acids precipitate during longer holding times and furthermore, the precipitated nucleic acids may irreversibly stick to the walls of the container which comprises the sample what considerably reduces the nucleic acid yield. The inventors now surprisingly found that the incorporation of a chelating agent in the resuspended sample considerably reduces the formation of precipitates and furthermore, prevents the adherence of the precipitate to the walls of the container comprising the resuspended sample which comprises the chaotropic agent. Thereby, a loss in the nucleic acid yield can be efficiently reduced. Thus, the teachings of the present invention allow the efficient isolation of nucleic acids, in particular RNA, with comparable yield and quality even if the resuspended samples prepared for nucleic acid isolation as described above are not directly processed but have different and/or prolonged holding times.

According to a second aspect, a method is provided for isolating nucleic acids from a sample, preferably a blood sample, wherein the nucleic acids are isolated from a plurality of samples and wherein variations in yield and quality of the nucleic acids that are isolated from said plurality of samples which result from that the plurality of samples prepared for isolation have diverging holding times before the nucleic acids are isolated from the prepared samples are thereby reduced that the samples prepared for isolation comprise at least one chaotropic agent and at least one chelating agent.

According to a third aspect, the present invention pertains to the use of a chelating agent in order to prevent or reduce the formation of a precipitate that attaches to the container wall of a sample comprising at least one chaotropic agent and nucleic acids. As discussed above, prolonged holding times of respective samples result in the formation of a precipitate, that sticks to the container wall comprising the chaotropic agent containing sample, thereby severely reducing the nucleic acid yield. Thus, the addition of the chelating agent as is taught by the present invention has the advantageous effect that the formation of a respective precipitate is reduced or even completely prevented. Thus, nucleic acids can be isolated with good yield and quality, even if the holding time between the preparation of the samples for isolation and the actual isolation is increased. This provides particular advantages if the technology of the present invention is used in order to isolate nucleic acids in automated processes wherein a large number of samples is prepared for nucleic acid isolation but wherein only a portion of the prepared samples can be processed batchwise on the automated system. Thus, the teachings of the present invention ensure substantially uniform isolation results with respect to quality and yield even if the holding time between different samples varies and/or is prolonged, what is in particular advantageous for challenging fields such as the isolation of nucleic acids for the medical and/or diagnostic field.

Other objects, features, advantages and aspects of the present application will become apparent to those skilled in the art from the following description and appended claims. It should be understood, however, that the following description, appended claims, and specific examples, while indicating preferred embodiments of the application, are given by way of illustration only. Various changes and modifications within the spirit and scope of the disclosed invention will become readily apparent to those skilled in the art from reading the following.

DETAILED DESCRIPTION OF THE INVENTION

Figure 1:
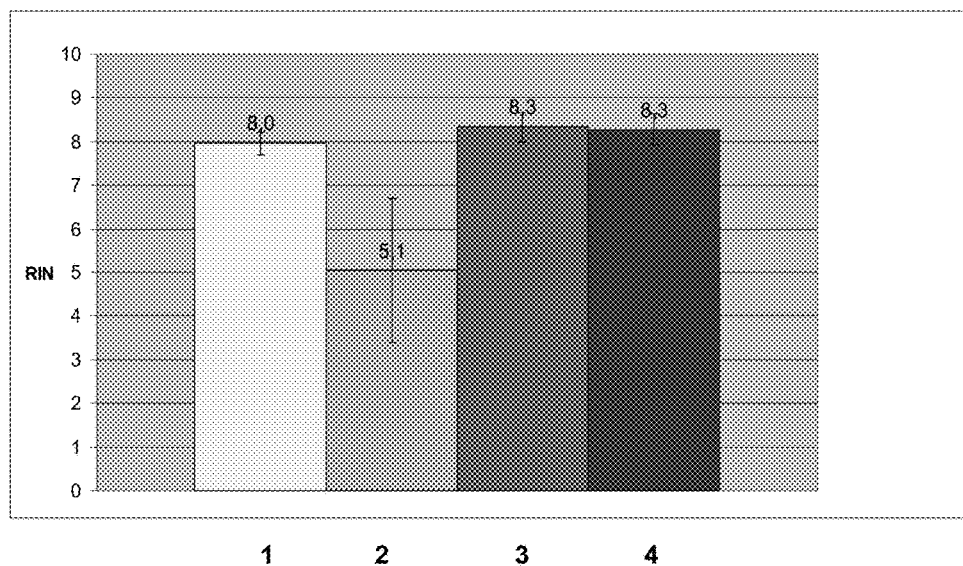
FIG. 1 is a graph showing RIN values (RNA integrity number) of RNA isolated from blood samples as described in Example 1.

The present invention is based on the finding that differences in nucleic acid quality and yield that are attributable to different holding times between sample preparation and actual nucleic acid isolation can be reduced by incorporating at least one chaotropic agent and at least one chelating agent into the sample that is prepared for nucleic acid isolation.

According to a first aspect, the present invention provides a method for isolating nucleic acids from a sample, preferably a blood sample, comprising the following steps:

a) obtaining a sample which has been stabilised by the use of at least one cationic detergent, wherein the cationic detergent has formed complexes with the nucleic acid;
b) obtaining the complexes optionally together with other sample components from the stabilised sample, wherein said complexes comprise the nucleic acid to be isolated;
c) resuspending the complexes and optionally adding one or more additives before, during and/or after resuspension, thereby obtaining a resuspended sample comprising at least
    i) the nucleic acid to be isolated;
    ii) at least one chaotropic agent; and
    iii) at least one chelating agent;
and
d) isolating nucleic acid from the resuspended sample.

The individual steps of the method will be explained in further detail:

In step a) a sample is obtained which has been stabilised by the use of at least one cationic detergent. E.g. the sample can be stabilised by contacting the sample with at least one cationic detergent. The cationic detergent supports the lysis the cells contained in the sample and forms complexes with the released nucleic acid. The nucleic acids are thereby stabilised. The use of cationic detergents for stabilising a sample, in particular a blood sample, is described in the prior art (see e.g. EP 1 031 626 and WO 02/00599, herein incorporated by reference) and will be described in further detail below. Respective stabilised samples can be e.g. obtained at one facility, e.g. a hospital and shipped to a second facility, e.g. a laboratory, wherein the samples are further processed and wherein the nucleic acids are isolated from the stabilised sample.

In step b) the complexes are obtained from the stabilised sample. Said complexes comprise the nucleic acid to be isolated. Said complexes also comprise the cationic detergent that was used for stabilising the sample. Said complexes can be obtained e.g. by sedimentation or filtration. Thereby, usually other sample components such as proteins and cell debris are also obtained together with the nucleic acid containing complexes. Preferably, the complexes are obtained in form of a pellet. A respective pellet can be e.g. obtained by centrifuging the sample and discarding the supernatant thereby obtaining a sample comprising the complexes comprising the nucleic acids and the cationic detergents. Depending on the type of sample to be processed, the respective pellet usually also comprises further sample components such as proteins and/or cell debris. This is in particular the case when processing complex samples such as e.g. whole blood or samples derived from blood such as serum or plasma. Suitable methods for separating the complexes e.g. by obtaining them in form of a pellet from the stabilized samples are also described in EP 1 031 626 paragraph [51] et seq, herein incorporated by reference. Obtaining the complexes, e.g. in form of a pellet, has the advantage that the subsequent nucleic acid isolation that is performed in step d) can be performed in smaller volumina what is cost-efficient as less reagents are necessary for nucleic acid isolation and furthermore, provides an important advantage when using automated methods for nucleic acid isolation because many automated systems are limited with respect to the volume they can process.

In step c) the complexes and optional other sample components, which are preferably obtained in form of a pellet, are resuspended, thereby obtaining a resuspended sample. Said resuspended sample comprises the nucleic acid to be isolated, the cationic detergent and optionally further sample components such as e.g. proteins and/or cell debris that were collected together with the complexes. Furthermore, optionally further additives can be added either before, during or after resuspension such as e.g. a chaotropic agent and/or a protein degrading compound. Herein, we refer to the resuspended complexes including optional further sample components and/or optional additives that were added before, during and/or after resuspension as "resuspended sample". According to the invention, the resuspended sample comprises at least one chaotropic agent. Preferably, the chaotropic agent is added as separate additive after the complexes were resuspended to provide a resuspended sample comprising a chaotropic agent. This order is preferred because the chaotropic agent might hamper the actual resuspension process of the complexes, in particular if the complexes are obtained in form of a pellet. Preferably, the chaotropic agent is added to the resuspended complexes in form of an aqueous solution as is described below in order to generate a resuspended sample comprising inter alia the nucleic acids and the chaotropic agent. As discussed above, the chaotropic agent protects the nucleic acids, in particular RNA, from degradation, thereby increasing the quality of the isolated nucleic acids. As is shown in the examples, if a chaotropic agent is comprised in the resuspended sample this has the effect that nucleic acids, in particular RNA, can be obtained with comparable quality even if the holding time varies and e.g. is extended between step c) and step d). Therefore, the isolation results obtained for different samples having different holding times between step c) and step d) are more uniform and thus comparable when using the method according to the present invention. However, the chaotropic agent not only has beneficial effects with respect to the preservation of the nucleic acid integrity, but also causes problems. During longer holding times it causes the formation of precipitates that can stick to the wall (the term "wall" also includes the bottom) of the container which comprises the resuspended sample. This precipitate formation and adherence to the container wall that is observed if a chaotropic agent is included in the resuspended sample reduces the yield of nucleic acids (DNA and/or RNA) that can be isolated from the resuspended sample. As is shown by the examples, the yield can even be reduced by up to 30% or even more, if the resuspended samples rest for a prolonged holding time between step c) and step d). This problem is overcome by the teachings of the present invention by additionally including at least one chelating agent in the resuspended sample. The chelating agent surprisingly reduces the formation of insoluble precipitates and also reduces the adherence of said precipitates to the container wall, thereby efficiently reducing the loss of nucleic acids during extended holding times between step c) and step d). The chelating agent can be added prior, during or after resuspension of the complexes in order to reduce respectively prevent the formation of precipitates that reduce the nucleic acid yield. Preferably, the chelating agent is added prior to the addition of the chaotropic agent. If the chelating agent is added after resuspension of the complexes, it should be added basically directly after resuspension in order to ensure that it can exhibit its beneficial effects described above. It should be added within one hour, preferably within 30 min, more preferably within 15 min, more preferably within 10 min, more preferably within 5 min, most preferably within 3 min.

Optionally, the method may comprise further treatment steps in order to prepare the resuspended sample for step d). Examples of respective additional steps are described in further detail below.

In step d), the nucleic acids are isolated from the resuspended sample. Here, basically any nucleic acid isolation method can be used. Suitable nucleic acid isolation methods are known in the prior art and include but are not limited to extraction, solid-phase extraction, silica-based purification methods, nucleic acid isolation procedures using chaotropic agents and/or at least one alcohol and a nucleic acid binding solid phase, magnetic particle-based purification, phenol-chloroform extraction, chromatography, anion-exchange chromatography (using anion-exchange surfaces), electrophoresis, filtration, precipitation, chromatin immunoprecipitation and combinations thereof. Preferably, the nucleic acids are isolated in step d) using an automated system. Preferably, the nucleic acids are isolated from a plurality of samples. The plurality of samples can be processed batchwise. The holding time may vary between individual batches, because the present invention ensures comparable nucleic acid isolation results even if the holding time significantly varies between batches. Suitable methods and holding times are also described below.

The advantages of the respective method were explained above and are also demonstrated by the examples. A loss in quality and/or quantity of the isolated nucleic acids that are attributable to longer holding times between step c) and step d) can be efficiently avoided due to the modified resuspension step taught by the present invention. Therefore, the present method provides more flexibility with respect to the allowable holding times between steps c) and d) what is in particular beneficial if the method according to the present invention is performed on an automated system, wherein, preferably, a plurality of samples are processed in a batchwise procedure.

Preferred embodiments of the method according to the present invention and of the steps a) to d) are described subsequently.

According to one embodiment, a resuspension solution is added in step c) to the obtained complexes wherein said resuspension solution comprises a salt, preferably a non-chaotropic salt. As salt, several salts can be used including but not being limited to ammonium salts and alkali metal salts, preferably ammonium acetate, ammonium sulphate, KCl or NaCl. Preferably, an ammonium salt is used. Preferably, the chelating agent is comprised in the resuspension solution. This embodiment is easy in handling and furthermore, also ensures that the chelating agent can immediately exhibit it's beneficial effects on the resuspended sample in that it prevents the formation of precipitates and/or adherence of the nucleic acids to the container walls when the resuspended sample when the chaotropic agent is added in order to protect the nucleic acid. As discussed above, it is preferred to add the chaotropic agent after the complexes were resuspended and accordingly, after the resuspension solution was added. Accordingly, the resuspension solution preferably does not comprise a chaotropic agent, in particular does not comprise a chaotropic salt and accordingly, is a non-chaotropic resuspension solution. According to one embodiment, the resuspension solution comprises the chelating agent in a concentration of at least 1 mM, at least 5 mM, preferably at least 7.5 mM, more preferred at least 10 mM, at least 15 mM or at least 20 mM. Preferably, the concentration range is selected from 1 mM to 150 mM, 5 mM to 100 mM, 5 mM to 75 mM, 7.5 mM to 65 mM, 7.5 mM to 50 mM and 10 mM to 30 mM. As was shown by examples, already a low concentration of a chelating agent such as EDTA is sufficient in order to achieve the beneficial effect on the precipitate formation. In some embodiments to use a lower to medium concentration of the chelating agent e.g. in a range of 1 mM to 50 mM, preferably 5 mM to 30 mM or 7.5 mM to 20 mM. To use lower concentrations of the chelating agent reduces the risk that the chelating agent is carried over into the eluate while still achieving the beneficial effect on the precipitate formation. The chelating agent may also be added separately from the resuspension solution, e.g. in liquid or solid form.

According to one embodiment, the chelating agent is added in a concentration so that the resuspended sample comprises the chelating agent in a concentration of at least 0.5 mM, at least 2.5 mM, preferably at least 3.5 mM, more preferred at least 5 mM, at least 7.5 mM or at least 10 mM. Preferably, the chelating agent is added in a concentration so that the resuspended sample comprises the chelating agent in a concentration selected from 0.5 mM to 100 mM, 2.5 mM to 75 mM, 2.5 mM to 60 mM, 3.5 mM to 50 mM, 3.5 mM to 30 mM, 3.5 mM to 25 mM, 3.5 mM to 20 mM, 5 mM to 15 mM and 5 mM to 10 mM.

The chelating agent that is used according to the present invention prevents or reduces the formation of a precipitate and/or the adherence of precipitate to the container when comprised in the resuspended sample. According to one embodiment, the chelating agent is an organic ligand, which is capable of forming two or more separate coordinate bonds to a metal cation and comprises at least one nitrogen atom as nucleophilic coordinating atom. According to one embodiment, the chelating agent is an organic ligand, which is capable of forming two or more separate coordinate bonds to a metal cation and comprises at least four nucleophilic coordinating atoms. According to one embodiment, the chelating agent is an organic ligand, which is capable of forming two or more separate coordinate bonds to a metal cation and comprises at least four carboxylic groups. According to one embodiment, the chelating agent is an organic ligand, which is capable of forming two or more separate coordinate bonds to a metal cation, the stability constant of the resulting complex being at least $10^4$ $M^{-1}$ in case of calcium as metal cation. Chelating agents according to the present invention include, but are not limited to diethylenetriaminepentaacetic acid (DTPA), ethylenedinitrilotetraacetic acid (EDTA), ethylene glycol tetraacetic acid (EGTA) and N,N-bis(carboxymethyl)glycine (NTA). According to a preferred embodiment, EDTA is used. As used herein, the term "EDTA" indicates inter alia the EDTA portion of an EDTA compound such as, for example, $K_2$EDTA, $K_3$EDTA or $Na_2$EDTA.

As discussed above, the chelating agent has several beneficial effects. It reduces the precipitate formation and in particular the binding of the nucleic acid containing precipitate to the container comprising the resuspended sample which comprises a chaotropic agent, thereby reducing or even preventing a loss in nucleic acid yield, in particular if the resuspended sample stands for a prolonged times before the nucleic acids are isolated from the resuspended sample (e.g. more than 0.1 h, more than 0.2 h, more than 0.3 h, in particular more than 0.5 h, more than 0.75 h, more than 1 h, more than 1.25 h, more than 1.5 h, more than 1.75 h, more than 2 h, more than 2.5 h or more than 3 h or more than in a range from 0.1 h to 12 h, 0.5 h to 11 h, 0.75 h to 10 h, 1 h to 9 h, 1.25 h to 8.5 h, 1.5 h to 8 h, 1.75 h to 7.5 h, 1.25 h to 7 hours, 1.5 h to 6.5 h, 1.75 h to 6 h or 2 h to 5.5 h). Thereby, the chelating agent reduces variations in the nucleic acid isolation efficiency and/or quantity attributable to different and in particular prolonged holding times between step c) and d).

According to one embodiment, the chelating agent that is used to prevent or reduce the formation of a nucleic acid containing precipitate and/or the adherence of precipitate to the container when comprised in the resuspended sample is no classical buffering agent such as citrate. However, a buffering agent may be and is also preferably comprised in the resuspended sample in addition to the chelating agent that is used to prevent or reduce the formation of the precipitate and/or the adherence of precipitate to the container. A respective buffering agent may be e.g. comprised in the resuspension solution.

As discussed above, in order to preserve the integrity of the nucleic acids comprised in the sample, in particular RNA, and in particular during longer holding times of the resuspended sample, a chaotropic agent is incorporated in and thus comprised in the resuspended sample. This is particularly advantageous when isolating RNA which is very sensitive to the omnipresent RNases. As is demonstrated by the examples, incorporating a chaotropic agent into the resuspended sample considerably improves the quality of the isolated RNA, in particular if the sample stands for a longer time between steps c) and d) as is often the case when isolating nucleic acids from a plurality of samples using an automated system and in particular, if a batchwise procedure is used to process the plurality of samples.

Any chaotropic agent can be used in step c) that causes disorder in a protein or nucleic acid by, for example, but not limited to altering the secondary, tertiary or quaternary structure of a protein or a nucleic acid while leaving the primary structure intact. Preferably, a chaotropic salt is used. Preferred chaotropic agents include but are not limited to chaotropic salts comprising e.g. thiocyanate, isothiocyanate, perchlorate, trichloroacetate, trifluoroacetate or iodide and/or comprising guanidinium and are preferably selected from guanidinium hydrochloride, guanidinium thiocyanate, guanidinium isothiocyanate, sodium thiocyanate, sodium iodide, sodium perchlorate, sodium trichloroacetate, sodium trifluroacetate, urea and the like. Preferably, the chaotropic agent is GTC or GITC or an equally strong chaotropic agent. Respective strong chaotropic agents are very efficient in protecting the nucleic acid, in particular RNA, from degradation. However, respective strong chaotropic agents strongly induce the precipitate formation and adherence of the precipitate to the container wall described above. According to one embodiment, the resuspended sample comprises the chaotropic agent in a concentration selected from the group consisting of 0.1 up to the saturation limit, 0.2 to 6M, 0.1 M to 4 M, 0.5M to 3M, 0.75M to 2.5M, most preferred at least 1M. As is shown in the examples, using a respective concentration is useful to efficiently preserve the integrity of the incorporated nucleic acids. The at least one chaotropic agent may be added in step c) in form of a separate solution. Said separate solution preferably comprises a chaotropic salt, e.g. a guanidinium salt, a buffer and/or a chelating agent. Preferably, said buffer comprises sodium citrate.

The pH value of the resuspended sample preferably lies in a range that is selected from 5 to 10, 5.5 to 9.5, 6 to 9, 6.5 to 8.5 and preferably 7 to 8. In a pH range of 5 to 8.5, pellets obtained from blood samples were particularly well resuspended. Therefore, according to one embodiment, a resuspension solution is added in step c) to the complexes, preferably the pellet comprising the cationic detergent and the nucleic acids that which has a pH value that achieves, with the added amount, a pH value in the resuspended sample that lies in the above defined pH range. According to one embodiment, the pH value of the resuspension solution lies in a pH range that is selected from 5 to 10.5, 5.5 to 10, 5.7 to 10, 6 to 9.7, 6.3 to 9.5, 6 to 9 and 6 to 8.5. Preferably, the pH range lies with a range of 5.7 to 10, more preferred 6 to 9. Here, the achieved nucleic acid yield was optimal.

According to one embodiment, a protein degrading compound is added in step c) and thus is comprised in the resuspended sample. It was found by the inventors that the addition of a protein degrading compound supports the effects of the chelating agent. Thus, including a protein degrading compound in the resuspended sample is beneficial in order to prevent the precipitate formation and the adherence of nucleic acid containing precipitates to the container walls. According to a preferred embodiment, the protein-degrading compound is a proteolytic enzyme. A proteolytic enzyme refers to an enzyme that catalyzes the cleavage of peptide bounds, for example in proteins, polypeptides, oligopeptides and peptides. Exemplary proteolytic enzymes include but are not limited to proteinases and proteases in particular subtilisins, subtilases, alkaline serine proteases and the like. Subtilases are a family of serine proteases, i.e. enzymes with a serine residue in the active side. Subtilisins are bacterial serine protease that has broad substrate specificities. Subtilisins are relatively resistant to denaturation by chaotropic agents, such as urea and guanidine hydrochloride and anionic detergents such as sodium dodecyl sulfate (SDS). Exemplary subtilisins include but are not limited to proteinase K, proteinase R, proteinase T, subtilisin, subtilisin A, QIAGEN Protease and the like. Discussions of subtilases, subtilisins, proteinase K and other proteases may be found, among other places in Genov et al., Int. J. Peptide Protein Res. 45: 391-400, 1995. Preferably, the proteolytic enzyme is proteinase K. Incorporating a protein-degrading compound such as in particular a proteolytic enzyme in the resuspended sample has the advantage that the resuspended sample is also pre-digested during the holding time before the nucleic acids are isolated in step d). In non-limiting aspects, the proteolytic enzyme is comprised in the resuspended sample in a concentration between about 0.05 mg/ml to about 10 mg/ml. In other embodiments the range can be between from about 0.1 mg/ml to about 5 mg/ml, or between about 0.2 mg/ml to about 1.0 mg/ml. It was found by the inventors that the protein-degrading compound such as in particular a proteolytic enzyme supports the prevention of precipitate formation and adherence of precipitate to the container walls. This effect was seen, even if the sample was not incubated under conditions that are optimal for the performance of the proteolytic enzyme (e.g. heating and agitation).

In order to efficiently prepare the resuspended sample for the nucleic acid isolation in step d) it is preferred to thoroughly digest the resuspended sample prior to isolating the nucleic acids. Here, different options exist that may be used in conjunction with the present invention. Some non-limiting options are subsequently described.

According to one embodiment, which is preferred, a proteolytic enzyme is included in the resuspended sample. As discussed above, the proteolytic enzyme may be directly added in step c) either before, during or after, preferably directly after, resuspension of the complexes and thereby is included in the resuspended sample. According to one embodiment, the respectively prepared resuspended sample is then incubated under conditions that allow at least the partial digestion of the sample. Digestion may e.g. occur during the holding time of the resuspended sample e.g. at room temperature. Thereby, the resuspended sample is—depending on the holding time—at least partially digested prior to step d). Digestion may be incomplete during the holding time between step c) and d). In order to ensure an efficient nucleic acid isolation in step d), a thorough digestion of the resuspended sample is preferred. Thus, according to one embodiment, after the holding time of the resuspended sample and thus, preferably in the initial step of the nucleic acid isolation performed in step d), the resuspended sample is incubated in step d) under conditions that support the digestion of the resuspended sample, preferably under heating and agitation for at least 3 min, preferably at least 5 min. If no proteolytic enzyme has been added in step c), a proteolytic enzyme would be added in step d) in order to allow an efficient digestion of the resuspended sample. It is also within the scope of the present invention to add an additional amount or a further (e.g. a different) proteolytic enzyme or protein-degrading compound in step d) even if a proteolytic enzyme was already included in the resuspended sample in step c).

According to a preferred embodiment, a proteolytic enzyme is comprised in the resuspended sample that is obtained in step c). During the holding time of the resuspended sample, the proteolytic enzyme can at least partially digest the resuspended sample even under non-optimal incubation conditions (e.g. at room temperature). In order to ensure a high efficiency of the digestion, the resuspended sample is preferably incubated after the holding time in the initial step of the nucleic acid isolation that is performed in step d) under conditions that promote the digestion of the sample, e.g. heating and agitation.

According to one embodiment, the conditions that allow the digestion of the sample and which preferably are used in step d) comprise one or more of the following
a) heating,
b) agitation,
c) the presence of salts,
d) a pH value of between 6 to 9 and/or
e) an incubation period of at least 3 min, preferably at least 5 min, most preferred for at least 10 min.

Preferably, said incubation step is performed under heating. Preferably, the resuspended sample is heated at least to a temperature of 35° C., at least 40° C., or at least 50° C. and preferably is heated to a temperature of at least 55° C. during incubation. Using respective higher temperatures during incubation is in particularly favourable if a proteolytic enzyme such as proteinase K is used as protein-degrading compound that shows its optimal, respective highest activity at higher temperatures. Under such conditions, the digestion of the resuspended sample is promoted. Of course, a temperature should be used wherein the proteolytic enzyme is active. Furthermore, it is preferred that the said incubation step is performed while agitating the resuspended sample. Non-limiting examples of agitation include shaking, stirring, mixing, or vibrating. In certain aspects, agitation comprises shaking. The shaking can be one, two, or three dimensional shaking. A variety of shaking or agitating devices can be used. Non-limiting examples include the Thermomixer (Eppendorf), TurboMix (Scientific Industries), Mo Bio Vortex Adapter (Mo Bio Laboratories), Microtube holder vortex adapter (Troemner), and the Microtube foam rack vortex attachment (Scientific Industries). Agitating can be performed for example in a mixer with at least 50 rpm, at least 100 rpm, at least 200 rpm or at least 500 rpm. Preferably, heating and agitation is simultaneously performed, for example by using a thermomixer or an equivalent apparatus that allows simultaneous heating and agitation. When using at least one proteolytic enzyme as protein-degrading compound, incubation conditions are used that ensure that said enzyme works efficiently and is catalytically active. The conditions depend on the proteolytic enzyme used and are known, respectively determinable by the skilled person. Preferably, the incubation is performed in the presence of salts and/or ions that promote and/or maintain the activity of the proteolytic enzyme. Suitable salts include but are not limited to NaCl, KCl, $MgCl_2$, or $CaCl_2$ or chaotropic agents such as chaotropic salts.

The above described conditions are particularly favourable when using a proteolytic enzyme as protein-degrading compound and said conditions promote the digestion of the resuspended sample. As discussed above, a digestion of the resuspended sample under respective conditions is preferably performed as initial step in nucleic acid step d).

Furthermore, as at least one chaotropic agent is included in the resuspended sample in order to preserve the integrity of the comprised nucleic acid, in particular the RNA, the digestion is performed in the presence of at least one chaotropic agent, preferably a chaotropic salt. It is also within the scope of the present invention to add a further amount or type of chaotropic agent at the time wherein the digestion is performed. For this purpose a digestion solution can be added which comprises at least one chaotropic agent, which may be the same or different than the one(s) that is/are included in the resuspended sample. Said digestion solution may also comprise additional compounds such as e.g. detergents and salts that promote the digestion and/or preserve the comprised nucleic acid. Any chaotropic agent can be used for that purpose that causes disorder in a protein or nucleic acid by, for example, but not limited to altering the secondary, tertiary or quaternary structure of a protein or a nucleic acid while leaving the primary structure intact. Preferred chaotropic agents that can be used during incubation with the at least one protein-degrading compound are chaotropic salts which include but are not limited to guanidinium hydrochloride, guanidinium thiocyanate, guanidinium isothiocyanate, sodium thiocyanate, sodium iodide, sodium perchlorate, sodium trichloroacetate, sodium trifluroacetate, urea and the like.

The incubation with the at least one protein-degrading compound to digest the resuspended sample is usually performed at a pH value that does not lead to a degradation of the comprised nucleic acid. Furthermore, when using a proteolytic enzyme as protein-degrading compound, a pH value should be used wherein the proteolytic enzyme is active. Preferably, the incubation with the at least one protein-degrading compound for digesting the resuspended sample is performed at a pH between 4.3 to 9, 6 to 8 and, preferably, is performed at a neutral pH value.

As discussed above, according to one embodiment, the proteolytic enzyme is included in the resuspended sample. In this embodiment, digestion already occurs during the holding time of the resuspended sample between step c) and d). However, as the resuspended samples may have different holding times prior to step d) and furthermore, digestion might not be complete under the conditions that are present during the holding time, it is preferred to additionally incubate the resuspended sample after the holding time under conditions that promote the digestion of the sample in the initial step of the nucleic acid isolation that is performed in step d).

According to a preferred embodiment, the incubation for digesting the resuspended sample is performed under heating, agitation, in the presence of chaotropic agents, a pH of 5 to 9, preferably 6 to 8, preferably a neutral pH, and for an incubation period of at least 3, preferably at least 5 minutes. In order to ensure efficient degradation of the proteins in step d), the resuspended sample should be incubated in step d) for a period of at least 3 minutes, preferably at least 5 minutes at elevated temperatures preferably above 50° C. in order to ensure efficient protein degradation. According to a preferred embodiment, the incubation is performed for at least 5 minutes, preferably for at least 10 minutes.

After optionally, but preferably digesting the resuspended sample as described above as initial step of the nucleic acid isolation procedure in step d), the nucleic acid can be e.g. bound to a solid phase and the nucleic acid can be optionally eluted therefrom. Preferred embodiments are described below.

As solid phase, any material that is capable of binding nucleic acids that are present in or are released from a sample can be used and include a variety of materials that are capable of binding nucleic acids under suitable conditions. Exemplary solid phases that can be used in conjunction with the present invention include, but are not limited to, compounds comprising silica, including but not limited to, silica particles, silicon dioxide, diatomaceous earth, glass, alkylsilica, aluminum silicate, and borosilicate; nitrocellulose; diazotized paper; hydroxyapatite (also referred to as hydroxyl apatite); nylon; metal oxides; zirconia; alumina; polymeric supports, diethylaminoethyl- and triethylaminoethyl-derivatized supports, hydrophobic chromatography resins (such as phenyl- or octyl Sepharose) and the like. The term solid phase is not intended to imply any limitation regarding its form or design. Thus, the term solid phase encompasses appropriate materials that are porous or non-porous; permeable or impermeable; including but not limited to membranes, filters, sheets, particles, magnetic particles, beads, gels, powders, fibers, and the like. According to one embodiment, the surface of the solid phase such as e.g. the silica solid phase is not modified and is, e.g., not modified with functional groups.

According to a preferred embodiment, a solid phase comprising silica is used. Silica based nucleic acid isolation methods are broadly used in the prior art. The solid phase comprising silica may e.g. have the form of a filter, fibres, membrane or particles. In particular preferred is the use of silica particles that can be used in form of beads and which preferably have a particle size of about 0.02 to 30 µm, more preferred 0.05 to 15 µm and most preferred of 0.1 to 10 µm. To ease the processing of the nucleic acid binding solid phase, preferably magnetic silica particles are used. The magnetic silica particles may e.g. be ferrimagnetic, ferromagnetic, paramagnetic or superparamagnetic. Suitable magnetic silica particles are for example described in WO 01/71732, WO 2004/003231 and WO 2003/004150. Other magnetic silica particles are also known from the prior art and are e.g. described in WO 98/31840, WO 98/31461, EP 1 260 595, WO 96/41811 and EP 0 343 934 and also include for example magnetic silica glass particles.

According to one embodiment, binding is performed under conditions having one or more, preferably at least two of the following characteristics:
 a) binding is performed in the presence of at least one chaotropic agent,
 b) binding is performed in the presence of at least one alcohol,
 c) binding is performed in the presence of at least one detergent,
 d) binding is performed under conditions that promote binding of the nucleic acids, in particular the RNA, and/or
 e) binding is performed under conditions that promote binding of small nucleic acids, in particular small RNA species.

According to one embodiment, the binding of the nucleic acids to the solid phase is performed in step d) in the presence of at least one chaotropic agent, preferably a chaotropic salt and/or in the presence of at least one alcohol. As discussed above, also a mixture of chaotropic agents can be used. The concentration of the chaotropic agent or mixture of chaotropic agents that are used during binding may lie in a range of 0.05M up to the saturation limit. Preferred concentration ranges lie, depending on the chaotropic agent used, within 0.1M to 7M, 1M to 7M, 1.5M to 6M and 2M to 4M. Suitable chaotropic agents are in particular chaotropic salts and include but are not limited to guanidinium hydrochloride, guanidinium thiocyanate, guanidinium isothiocyanate, sodium thiocyanate, sodium iodide, sodium perchlorate, sodium trichloroacetate, sodium trifluoroacetate, urea and the like and in particular preferred are guanidinium hydrochloride, guanidinium thiocyanate and guanidinium isothiocyanate. As discussed above, the resuspended sample already comprises at least one chaotropic agent that has been added in order to preserve the integrity of the nucleic acids in the resuspended sample during longer holding times between step c) and step d). Thus, it is not necessary to additionally add a chaotropic agent in order to allow binding of the nucleic acids to the solid phase. However, it is also within the scope of the present invention to additionally add at least one chaotropic agent in step d) e.g. in form of an aqueous binding solution.

As alcohol that can be used to promote binding, it is preferred to use short chained branched or unbranched alcohols with preferably one to 5 carbon atoms. Examples are methanol, ethanol, propanol, isopropanol and butanol. Also mixtures of alcohol can be used. The alcohol is preferably selected from isopropanol and ethanol, particularly well suitable is isopropanol when isolating RNA as target nucleic acid. Preferably, the method according to the present invention does not involve the use of phenol and/or chloroform.

The alcohol may be comprised in the binding mixture in a concentration of 10% v/v to 90% v/v, in particular 15% v/v to 80% v/v, 20% to 80% v/v. The binding mixture in particular comprises the resuspended sample and the solid phase and may optionally comprise further agents that were added to establish, respectively improve the binding conditions. For isolating total RNA which also comprises small RNA, it is beneficial to use an alcohol concentration of ≥30% v/v, preferably ≥40% v/v to ≤90% v/v, more preferred ≥50% v/v to ≤90% v/v or ≥60% v/v to ≤80% v/v during binding and thus in the binding mixture. Respective higher concentrations of alcohol improve the binding and thus the isolation of short nucleic acids (usually having a size respectively length of ≥500 nt or less), in particular small RNA species. Most preferred is an alcohol concentration of ≥40% v/v to ≤90% v/v or ≥60% v/v to ≤80% v/v during binding when intending to isolate RNA which includes small RNA. These concentrations work particularly well if the chaotropic agent(s) is/are present in higher concentrations and when binding the nucleic acids to a silica surface.

Thus, according to one embodiment, the isolation in step d) is performed using binding conditions having one or more of the following characteristics to bind the nucleic acids to a solid phase:
- a) an alcohol concentration is used that is selected from the group consisting of 10% v/v to 90% v/v, 15% v/v to 90% v/v, 20% v/v to 85% v/v, 30% v/v to 80% v/v, 40% v/v to 85% v/v, 40% v/v to 80%, 40% v/v to 70%, ≥50% v/v to ≤80% v/v and ≥60% v/v to ≤80% v/v,
- b) a concentration of one or more chaotropic agents is used that is selected from the group consisting of 0.05M up to the saturation limit, 0.1M to 6M and 1M to 4M, and/or
- c) an alcohol concentration of at least 30% v/v, preferably at least 40% v/v and at least one chaotropic agent is used for binding RNA, including small RNAs to the solid phase.

To establish respective binding conditions, a binding solution which comprises e.g. the alcohol and the chaotropic agent can be added e.g. to the resuspended sample, preferably to the resuspended digested sample.

Optionally, one or more detergents can be added to the binding mixture to promote binding of the nucleic acid to the solid phase. Preferably, at least one ionic and/or at least one non-ionic detergent is added. Preferably, a non-ionic detergent is used in a concentration of at least 5%. Said detergent can be added, e.g., together with the binding solution or can be provided by the resuspended sample and/or the digestion solution if a respective digestion solution is added to promote the digestion, respectively lysis of the sample.

Furthermore, a buffer such as a biological buffer can be used for binding, respectively can be incorporated in the binding solution. Non-limited examples of biological buffers include but are not limited to HEPES, MES, MOPS, TRIS, BIS-TRIS Propane and others. Preferably, a Tris buffer is used in the binding solution.

Therefore, according to one embodiment, the nucleic acid isolation in step d) comprises the addition of a binding solution which comprises at least one alcohol and/or at least one chaotropic agent and optionally a biological buffer, preferably Tris, in order to establish the binding conditions that allow to bind the nucleic acid that are comprised in the resuspended sample to the solid phase. Optionally, the binding solution additionally comprises a detergent as is described above. However, the components can also be added separately to establish suitable binding conditions in the binding mixture. Preferably, the binding solution pH is in a range that includes 8. According to one embodiment, the pH of the binding solution is in the range from pH 7.0 to 9, preferably 7.5 to 8.5; most preferred the binding solution has a pH of 8.

According to one embodiment, one or more washing steps are performed in isolation step d) in order to further purify the isolated nucleic acids. According to one embodiment, one or more washing steps are performed while the nucleic acid is bound to the solid phase. For this purpose common washing solutions may be used. According to one embodiment, the solution used for washing comprises at least one chaotropic agent, at least one alcohol, at least one detergent and/or at least one buffering component. Chaotropic agents that can be used in the washing solutions include but are not limited to guanidinium hydrochloride, guanidinium thiocyanate, guanidinium isothiocyanate and sodium iodide. Furthermore, chaotropic salts can be used which comprise a chaotropic anion selected form the group consisting of trichloroacetate, perchlorate and trifluoroacetate. Examples of respective chaotropic salts are alkali salts like sodium perchlorate, sodium trichloroacetate and sodium trifluoroacetate. As alcohol, short chained branched or unbranched alcohols with preferably one to 5 carbon atoms can be used for washing, respectively in the washing solution. Examples are methanol, ethanol, propanol, isopropanol and butanol. Preferably, isopropanol and/or ethanol are used. Preferably, the washing solution comprises at least 50% alcohol and at least 1M chaotropic salt, preferably at least 2M chaotropic salt. Furthermore, the washing solution may comprise a detergent. Preferably, ionic and/or non-ionic detergents are used as detergent. Preferably, a non-ionic detergent is used in a concentration of at least 5%.

A further suitable washing solution which can be used alternatively or also in addition to the washing solutions described above comprises an alcohol and a biological buffer. Suitable alcohols and biological buffers are described above. Preferably, isopropanol or ethanol, most preferred ethanol is used for this second washing step. Preferably, ethanol is used in a concentration of at least 70% v/v, preferably at least 80% v/v. The biological buffer is preferably Tris at a pH of approx. 7 to 8. According to one embodiment, the solution used for washing comprises at least one chaotropic agent, at least one alcohol, at least one detergent and/or at least one buffering component.

In case it is desired to perform an elution step to elute the nucleic acids from the solid phase, elution can be performed for example with classical elution solutions such as water, elution buffers, in particular biological buffers such as Tris and preferably elution solutions are used that do not interfere with the intended downstream application. After elution, the eluate can be heat denatured. However, it is also within the scope of the present invention to release and thus elute the nucleic acids from the solid phase in step c) and/or e) by other elution means such as e.g. heating.

According to one embodiment, DNA as well as RNA is bound in step d) to a solid phase and thus is isolated according to the method of the present invention. As discussed above, the teachings of the present invention increase the overall nucleic acid yield while preserving the integrity of the nucleic acids.

According to one embodiment, the sample comprises at least one non-target nucleic acid and at least one target nucleic acid and the method aims at isolating predominantly the target nucleic acid. E.g. the non-target nucleic acid can be DNA and the target nucleic acid can be RNA or vice versa.

According to one embodiment, isolation step d) comprises several intermediate steps in order to allow the isolation of predominantly the target nucleic acid. According to one embodiment, isolation step d) comprises not only a sample digestion step (see above) but also an intermediate step that removes at least a portion of non-target nucleic acid. Preferably, the non-target nucleic acid is removed by binding at least a portion of the non-target nucleic acid under appropriate conditions to a solid phase and then separating the non-target nucleic acid bound to the solid phase from the remaining sample comprising the target nucleic acid. This can be achieved e.g. by the addition of a suitable solid phase under conditions wherein mainly the non-target nucleic acids are bound to the solid phase. Suitable methods for selectively removing a non-target nucleic acid from a target nucleic acid are for example described in EP 0 880 537 and WO 95/21849, herein incorporated by reference. If desired, said non-target nucleic acid may also be further used, e.g. further processed such as e.g. eluted from the solid phase.

However, it may also be discarded. When intending to isolate (only) RNA as target nucleic acid, the non-target nucleic acid is usually DNA.

In order to further reduce the amount of non-target nucleic acids in the isolated target nucleic acid, an intermediate step for degrading non-target nucleic acids using a suitable enzyme can be performed after at least the portion of the non-target nucleic acid was removed. It is also within the scope of the present invention to skip the removal step and to destroy non-target nucleic acids by using one or more appropriate enzymes only. Thus, according to one embodiment, isolation step d) comprises performing an enzymatic treatment in order to degrade (remaining) non-target nucleic acids. According to one embodiment wherein RNA is isolated as target nucleic acid, a DNase treatment is performed. As the conditions for performing a DNase digest are well known in the prior art, they do not need further description here. Basically the same applies when isolating DNA as target nucleic acid and accordingly when using an RNase for degrading RNA as non-target nucleic acid.

According to a preferred embodiment of the present invention wherein RNA is isolated from a sample comprising at least RNA and DNA, isolation step d) comprises the following steps
  i) removing at least a portion of the DNA from the resuspended and preferably digested sample, by binding DNA to a first solid phase and separating the DNA bound to said first solid phase from the remaining sample comprising the RNA,
  ii) binding the RNA to a second solid phase, wherein at least one chaotropic agent and at least one alcohol in a concentration 30% v/v is used during this binding step ii),
  optionally performing at least one washing step for washing the RNA bound to said second solid phase, and
  optionally eluting the RNA from said second solid phase.

Isolation step d) may also comprise additional steps, e.g. at least one additional enzymatic digestion step to digest remaining DNA and/or protein contaminations.

According to a preferred embodiment of the present invention wherein at least RNA is isolated from a sample comprising at least RNA and DNA, isolation step d) comprises the following steps:
  Obtaining the resuspended sample comprising a proteolytic enzyme and continuing the digestion of the resuspended sample preferably by incubating the resuspended sample for at least 5 min above room temperature preferably above 50° C. Suitable incubation conditions are described above, it is referred to the respective disclosure.
  Removing at least a portion of the DNA from the resuspended and digested sample, by binding DNA to a first solid phase and separating the DNA bound to said first solid phase from the remaining sample comprising the RNA. Thereby, the DNA can be removed. The removed DNA can be further processed, e.g. analysed or amplified. Optionally, the DNA is eluted from the first solid phase if a parallel isolation of RNA and DNA is of interest.
  Binding the RNA to a second solid phase, wherein at least one chaotropic agent and at least one alcohol in a concentration 30% v/v is used during this RNA binding step. Suitable binding conditions and in particular suitable concentration ranges for the chaotropic agent and the alcohol are described above, it is referred to the respective disclosure.
  Optionally performing at least one washing step for washing the RNA bound to said second solid phase. Details with respect to the washing step were described above, it is referred to the respective disclosure.
  Optionally performing a DNase digest and/or a digest using a proteolytic enzyme. Performing a DNase digest has the advantage that remaining traces of DNA can be efficiently removed. Performing a second protein digestion step is also advantageous in order to increase the purity of the isolated RNA. Preferably, the RNA is eluted prior to performing the DNase digest and the proteolytic enzyme is added after the DNase digest was performed and the reaction mixture is incubated in the presence of a chaotropic agent. Suitable digestion conditions are also described above. Preferably, proteinase K is used as proteolytic enzyme. Details with respect to said second protein digestion step and the associated advantages are described in EP 10 007 346.9. After the protein digestion step was performed, the RNA is re-bound to the second solid phase preferably by adding at least one chaotropic agent and at least one alcohol. Suitable binding conditions are described above, it is referred to the respective disclosure. Preferably, the same binding conditions are used that were used in the first RNA binding step. After rebinding, optionally one or more washing steps can be performed. Optionally the RNA is eluted from said second solid phase and optionally the eluted RNA is denatured by performing a heat treatment.

It is also within the scope of the present invention to perform additional intermediate steps than the ones described herein. However, according to certain embodiments, no additional steps other than the ones described herein are performed.

The sample from which the nucleic acids are to be isolated can be, respectively were according to one embodiment stabilised by contacting the sample with a stabilizing composition having one or more of the following characteristics:
  a) it comprises
    a) a cationic compound of the general formula:

$$Y^+R_1R_2R_3R_4X^-$$

wherein Y represents nitrogen or phosphor, preferably nitrogen
   $R_1R_2R_3$ and $R_4$ independently, represent a branched or unbranched $C_1$-$C_{20}$-alkyl group, a $C_6$-$C_{20}$-aryl group and/or a $C_6$-$C_{26}$ aralkyl group;
   X represents an anion of an inorganic or organic, mono- or polybasic acid; and
  b) at least one proton donor.

According to one embodiment, which is particularly preferred when RNA is isolated from a biological sample such as whole blood or blood products such as plasma or serum, the nucleic acids contained in the sample are stabilised preferably immediately after the biological sample has been taken from its natural environment in order to preserve the status quo of the nucleic acid population comprised in the sample, in particular the transcription pattern. This is particularly beneficial in the medical and diagnostic field.

Thus, according to one embodiment, after the sample was obtained it is preferably immediately mixed with a nucleic acid storage stabilization composition for stabilizing nucleic acids in said sample prior to isolating the nucleic acids therefrom. E.g. the sample can be collected in a suitable collection device, e.g. an evacuated blood collection tube, which comprises the stabilization composition. Thereby, the sample is immediately stabilized upon collection. According to one embodiment, said stabilization composition comprises
a) a cationic compound of the general formula:

$Y^+R_1R_2R_3R_4X^-$ wherein Y represents nitrogen or phosphor, preferably nitrogen $R_1R_2R_3$ and $R_4$ independently, represent a branched or unbranched $C_1$-$C_{20}$-alkyl group, a $C_6$-$C_{20}$-aryl group and/or a $C_6$-$C_{26}$ aralkyl group;

$X^-$ represents an anion of an inorganic or organic, mono- or polybasic acid; and b) at least one proton donor, wherein the proton donor is preferably present in the composition in a concentration of above 50 mM to saturation and wherein the proton donor is preferably selected from the group consisting of saturated aliphatic monocarboxylic acids, unsaturated alkenyl-carboxylic acids, saturated and/or unsaturated aliphatic $C_2$-$C_6$-dicarboxylic acids, aliphatic hydroxyl-di- and tricarboxylic acids, aliphatic ketocarboxylic acids, amino acids or the inorganic acids or the salts thereof, on their own or in combination.

Preferably, $R_1$ denotes a higher alkyl group with 12, 14 or 16 carbon atoms and $R_2$, $R_3$ and $R_4$ each represent a methyl group.

Preferably, the anion $X^-$ represents an anion of hydrohalic acids or anions of mono- or dibasic organic acids, most preferred the anion $X^-$ is selected from the group consisting of bromide, chloride, phosphate, sulphate, formate, acetate, propionate, oxalate, malonate, succinate or citrate.

Preferably, the proton donor is selected from the group consisting of saturated aliphatic monocarboxylic acids, unsaturated alkenyl-carboxylic acids, saturated and/or unsaturated aliphatic $C_2$-$C_6$-dicarboxylic acids, aliphatic ketocarboxylic acids, amino acids or the inorganic acids or the salts thereof, and combinations thereof. Preferably, the aliphatic monocarboxylic acid comprises a $C_1$-$C_6$-alkyl-carboxylic acid selected from the group consisting of acetic acid, propionic acid, n-butyric acid, n-valeric acid, isovaleric acid, ethyl-methyl-acetic acid (2-methyl-butyric acid), 2,2-dimethylpropionic acid (pivalic acid), n-hexanoic acid, n-octanoic acid, n-decanoic acid or n-dodecanoic acid (lauric acid) or mixtures thereof. Preferably, the aliphatic alkenyl-carboxylic acid is selected from the group consisting of acrylic acid (propenoic acid), methacrylic acid, crotonic acid, isocrotonic acid or vinylacetic acid or mixtures thereof. Preferably, the saturated aliphatic $C_2$-$C_6$-dicarboxylic acid is selected from the group consisting of oxalic acid, malonic acid, succinic acid, glutaric acid or adipic acid or mixtures thereof. Most preferred, the aliphatic dicarboxylic acid is oxalic acid or succinic acid or mixtures thereof. Preferably, the aliphatic hydroxy-di- and -tricarboxylic acids are selected from the group consisting of tartronic acid, D-(+), L-(-) or DL-malic acid, (2R, 3R)-(+)-tartaric acid, (2S, 3S)-(-)-tartaric acid, meso-tartaric acid and citric acid or mixtures thereof. Most preferred, the unsaturated dicarboxylic acid is maleic and/or fumaric acid or mixtures thereof. Preferably, the unsaturated tricarboxylic acid is aconitic acid. Preferably, the aliphatic ketodicarboxylic acids are mesoxalic acid or oxaloacetic acid, or mixtures thereof. Preferably, the amino acids are selected from the group consisting of aminoacetic acid (glycine), alpha-aminopropionic acid (alanine), alpha-amino-iso-valeric acid (valine), alpha-amino-iso-caproic acid (leucine) and alpha-amino-beta-methylvaleric acid (isoleucine), or mixtures thereof.

Preferably, the stabilising composition is present in an aqueous solution. Preferably, the cationic compound is comprised in a concentration in the range from 0.01 weight percent to 15 weight percent.

Suitable stabilising solutions are also described in detail e.g. in U.S. Pat. No. 7,270,953, herein incorporated by reference. As described above, the cationic compound comprised in the stabilisation composition forms complexes with nucleic acids comprised in the sample.

According to one embodiment, the stabilised sample does not comprise a chelating agent. According to another embodiment, it may comprise a chelating agent.

According to an alternative embodiment, the stabilization composition comprises a detergent which comprises under the used conditions a charged quarternary ammonium cation as polar head group and thus is or becomes cationic under the used stabilisation conditions. Accordingly, also an originally non-ionic detergent can be used for providing nucleic acid complexes, if the detergent is or becomes cationic during stabilisation, respectively complex formation. Thus, besides cationic detergents comprising a permanently charged head group also an originally ternary amine can be used as cationic detergent if provided in an acidic environment whereby the ternary amine incorporates a proton and become positively charged.

According to one embodiment, an amino surfactant having the following formula 2 is used as detergent in the stabilisation composition which is or becomes cationic under the used stabilisation conditions and thereby functions as cationic detergent:

R1R2R3N(O)x  (2)

wherein,
R1 and R2 each independently is H, C1-C20 alkyl residue, C6-C26 aryl residue or C6-C26 aralkyl residue, preferably H, C1-C6 alkyl residue, C6-C12 aryl residue or C6-C12 aralkyl residue,
R3 is C1-C20 alkyl group, C6-C26 aryl residue or C6-C26 aralkyl residue, X is an integer of 0 and 1.

According to one embodiment, x is 1 and R1 and R2 each independently is C1-C6 alkyl, and R3 is C1-C20 alkyl. According to a preferred embodiment, x is 0. According to one embodiment, said amino surfactant is selected from the group consisting of dodecylamine, N-methyldodecylamine, N, N-dimethyldodecylamine, N, N-dimethyldodecylamine N oxide and 4-tetradecylaniline. Preferably, said amino surfactant is comprised in a stabilisation composition which additionally comprises at least one proton donor, preferably an acid or acid salt to render a quarternary ammonium cation. According to one embodiment, the stabilization composition comprises at least one acid salt selected from the group consisting of maleic acid, tartaric acid, citric acid, oxalic acid, carboxylic acids and mineral acids. The total concentration of said acid salt in the stabilization composition may preferably range from 0.01 M to 1M.

Complex samples that are stabilised as is described above using a cationic detergent are a particular challenge for isolating nucleic acids due to the additives in the stabilising solution and the high protein content of the sample, in particular if the sample is a blood sample or a sample derived from blood. The method of the present invention overcomes these difficulties and allows the isolation of RNA including small RNA (if desired) with good yield and high purity from respectively stabilised samples and in particular from complex biological samples such as whole blood and blood products such as buffy coat, serum and/or plasma or tissue samples, in particular organ tissue samples e.g.

obtained from lung or liver. Therefore, the method of the present invention is particularly useful in the medical and in particular in the diagnostic field.

According to one embodiment, the resuspended sample comprising the nucleic acid, the at least one chaotropic agent, the at least one chelating agent and optionally the protein-degrading compound is put on hold between step c) and step d). Said holding time prior to isolating the nucleic acid in step d) may have a duration of more than 0.1 h, more than 0.25 h, more than 0.5 h, more than 0.75 h, more than 1 h, more than 1.5 h, more than 2 h, more than 2.5 h or more than 3 h hours and preferably lies in a range selected from 0.25 h to 12 h, 0.5 h to 11 h, 0.75 h to 10 h, 1 h to 9 h, 1.25 h to 8.5 h, 1.5 h to 8 h, 1.75 h to 7.5 h, 1.25 h to 7 hours, 1.5 h to 6.5 h, 1.75 h to 6 h and 2 h to 5.5 h.

As discussed above, the circumstance that samples are put on hold between the resuspension in step c) and the actual nucleic isolation step d) often occurs when processing a plurality of samples using an automated system. As discussed above, the samples are often manually prepared (e.g. by centrifuging the samples to obtain the pellet comprising the complexes comprising the cationic detergent and the nucleic acids and adding the resuspension chemistry) for nucleic acid isolation. Afterwards, the prepared, resuspended samples are placed into a robotic system for nucleic acid isolation. Said robotic systems may also execute the digestion step described above as they are often designed to perform heating and/or agitation steps. The method according to the present invention has particular advantages when processing a plurality of samples, in particular when using an automated system.

Thus, according to one embodiment, a plurality of samples is processed, wherein the holding time between step c) and step d) differs at least between some of the resuspended samples.

According to this embodiment, a plurality of samples is processed according to the present method up to step c). After resuspension in step c), a portion of said plurality of samples is further processed according to step d), while the remaining, resuspended samples are put on hold. These resuspended samples that were put on hold are then further processed according to step d), preferably after the nucleic acids were isolated from the first portion of resuspended samples.

Preferably, the plurality of samples is processed using an automated system which is capable of processing magnetic particles. Using magnetic particles to isolate nucleic acids from the resuspended sample in step d) is beneficial because of the simplified handling. Magnetic particles can be processed by the aid of a magnetic field. Suitable and preferred magnetic particles are described above. Here, different automated robotic systems exist in the prior art that can be used in conjunction with the present invention to process magnetic particles during nucleic acid isolation in step d). According to one embodiment, magnetic particles are collected at the bottom or the side of the reaction vessel and the remaining liquid sample is removed from the reaction vessel, leaving behind the collected magnetic particles to which the nucleic acids are bound. Removal of the remaining sample can occur by decantation or aspiration. Such systems are well known in the prior art and thus need no detailed description here. In an alternative system that is known for processing magnetic particles the magnet which is usually covered by a cover or envelope plunges into the reaction vessel to collect the magnetic particles. The magnetic particles that carry the bound nucleic acids can then be transferred for example into a new reaction vessel e.g. comprising further processing solutions such as e.g. a washing solution. As respective systems are well-known in the prior art and are also commercially available (e.g. QIAsymphony; QIAGEN), they do not need any detailed description here. In a further alternative automated system that is known for processing magnetic particles, the sample comprising the magnetic particles can be aspirated into a pipette tip and the magnetic particles can be collected in the pipette tip by applying a magnet e.g. to the side of the pipette tip. The remaining sample can then be released from the pipette tip while the collected magnet particles which carry the bound nucleic acids remain due to the magnet in the pipette tip. The collected magnetic particles can then be processed further. Such systems are also well-known in the prior art and are also commercially available (e.g. BioRobot EZ1, QIAGEN) and thus, do not need any detailed description here.

The term "sample" is used herein in a broad sense and is intended to include a variety of sources that contain nucleic acids. The sample may be a biological sample but the term also includes other, e.g. artificial samples which comprise nucleic acids. Exemplary samples include, but are not limited to, body fluids in general, whole blood; serum; plasma; red blood cells; white blood cells; buffy coat; swabs, including but not limited to buccal swabs, throat swabs, vaginal swabs, urethral swabs, cervical swabs, throat swabs, rectal swabs, lesion swabs, abcess swabs, nasopharyngeal swabs, and the like; urine; sputum; saliva; semen; lymphatic fluid; liquor; amniotic fluid; cerebrospinal fluid; peritoneal effusions; pleural effusions; fluid from cysts; synovial fluid; vitreous humor; aqueous humor; bursa fluid; eye washes; eye aspirates; plasma; serum; pulmonary lavage; lung aspirates; and tissues, including but not limited to, liver, spleen, kidney, lung, intestine, brain, heart, muscle, pancreas, cell cultures, as well as lysates, extracts, or materials obtained from any cells and microorganisms and viruses that may be present on or in a sample and the like. Materials obtained from clinical or forensic settings that contain nucleic acids are also within the intended meaning of the term sample. Furthermore, the skilled artisan will appreciate that lysates, extracts, or materials or portions thereof obtained from any of the above exemplary samples are also within the scope of the term sample. Preferably, the sample is a biological sample derived from a human, animal, plant, bacteria or fungi. In particular, the term "sample" refers to a nucleic acid containing sample which also comprises proteins. Preferably, the sample is selected from the group consisting of cells, tissue, bacteria, virus and body fluids such as for example blood, blood products such as buffy coat, plasma and serum, urine, liquor, sputum, stool, CSF and sperm, epithelial swabs, biopsies, bone marrow samples and tissue samples, preferably organ tissue samples such as lung and liver. Preferably, the sample is selected from whole blood and blood products such as buffy coat, serum or plasma.

The term "nucleic acid" or "nucleic acids" as used herein, in particular refers to a polymer comprising ribonucleosides and/or deoxyribonucleosides that are covalently bonded, typically by phosphodiester linkages between subunits, but in some cases by phosphorothioates, methylphosphonates, and the like. Nucleic acids include, but are not limited to all types of DNA and/or RNA, e.g. gDNA; circular DNA; circulating DNA; hnRNA; mRNA; noncoding RNA (ncRNA), including but not limited to rRNA, tRNA, lncRNA (long non coding RNA), lincRNA (long intergenic non coding RNA), miRNA (micro RNA), siRNA (small interfering RNA), snoRNA (small nucleolar RNA), snRNA (small nuclear RNA) and stRNA (small temporal RNA), piRNA (piwi interacting RNA), tiRNA (transcription initiation RNA), PASR (promoter associated RNA), CUT (cryptic unstable transcripts), extracellular or circulating RNA; fragmented nucleic acid; nucleic acid obtained from subcellular organelles such as mitochondria or chloroplasts; and nucleic acid obtained from microorganisms, parasites, or DNA or RNA viruses that may be present in a biological sample. Synthetic nucleic acid sequences that may or may not include nucleotide analogs that are added or "spiked" into a biological sample are also within the scope of the invention. Small RNA or the term small RNA species in particular refers to RNA having a length of less than 500 nt, 400 nt, 300 nt or 100 nt and includes but is not limited to miRNA, siRNA, other short interfering nucleic acids, snoRNAs and the like. According to one embodiment, the nucleic acid is RNA. The RNA may include small RNA species.

As becomes apparent from the described examples of samples that can be processed according to the method of the present invention, a sample may comprise more than one type of nucleic acid. Depending on the intended use, it may be desirous to isolate all types of nucleic acids from a sample ((e.g. DNA and RNA) or only certain types or a certain type of nucleic acid (e.g. only RNA but not DNA or vice versa or DNA and RNA are supposed to be obtained separately). All these variants are within the scope of the present invention. Suitable methods for isolating either DNA or RNA or both types of nucleic acids in parallel are known in the prior art and are also described above.

The present invention also pertains to a method for isolating nucleic acids from a sample, preferably a blood sample, wherein the nucleic acids are isolated from a plurality of samples and wherein variations in yield and quality of the nucleic acids that are isolated from said plurality of samples which result from that the plurality of samples prepared for isolation have diverging holding times before the nucleic acids are isolated from the prepared samples are thereby reduced that the samples prepared for isolation comprise at least one chaotropic agent and at least one chelating agent.

The sample is preferably stabilised by using a cationic detergent which forms a complex with the nucleic acid contained in the sample. Details with respect to the cationic detergent are described above, it is referred to the above disclosure. Preferably, the nucleic acid is RNA and the sample is or is derived from a body fluid, preferably whole blood, serum or plasma, most preferred whole blood. According to one embodiment, the nucleic acids are isolated according to the method described above. It is referred to the above disclosure which also applies here.

Furthermore, the present invention pertains to the use of a chelating agent for preventing the formation of a precipitate that interacts with the container wall of a sample comprising a chaotropic agent and a nucleic acid. The sample is preferably stabilised by using a cationic detergent which forms a complex with the nucleic acid contained in the sample. Details with respect to the cationic detergent are described above, it is referred to the above disclosure. Preferably, the nucleic acid is RNA and the sample is or is derived from a body fluid, preferably whole blood, serum or plasma, most preferred whole blood. The advantages of a respective use of a chaotropic agent and a chelating agent in particular with respect to the increase in nucleic acid quality and quantity due to the prevention of the precipitate formation and/or adherence to the container wall were described in detail above. Suitable and preferred embodiments of the chelating agent and concentrations thereof, the chaotropic agent and concentrations thereof, the cationic detergent, the nucleic acids and sample types are described above. It is referred to the above disclosure which also applies here.

This invention is not limited by the exemplary methods and materials disclosed herein, and any methods and materials similar or equivalent to those described herein can be used in the practice or testing of embodiments of this invention. Numeric ranges are inclusive of the numbers defining the range. The headings provided herein are not limitations of the various aspects or embodiments of this invention which can be read by reference to the specification as a whole. The term "solution" as used herein, in particular refers to a liquid composition, preferably an aqueous composition. It may be a homogenous mixture of only one phase but it is also within the scope of the present invention that a solution that is used according to the present invention comprises solid components such as e.g. precipitates. According to one embodiment, subject matter described herein as comprising certain steps in the case of methods or as comprising certain ingredients in the case of compositions, solutions and/or buffers refers to subject matter consisting of the respective steps or ingredients. It is preferred to select and combine preferred embodiments described herein and the specific subject-matter arising from a respective combination of preferred embodiments also belongs to the present disclosure.

EXAMPLES

The present invention is now illustrated by the following non-limiting examples:

Example 1

24 blood samples (2.5 ml) were collected per batch in PAXgene Blood RNA Tubes (which comprise a cationic detergent as stabilising agent). The samples were stabilized for 24 h at room temperature and were processed with the QIAsymphony PAXgene Blood RNA Kit, 2008 (QIAGEN) according to the manufacturer's instructions.

QIAsymphony PAXgene Blood RNA Kit

In the QIAsymphony PAXgene Blood RNA protocol (prior art), the stabilised samples are manually prepared in order to collect and resuspend the pellet which comprises the complexes comprising the cationic detergent and the nucleic acids. Said pellet is obtained by centrifugation and the supernatant is decanted. Afterwards, 300 µl of the resuspension buffer BR1 (QIAGEN) was added to the pellet and vortexed. The respectively manually prepared samples were then loaded on the QIAsymphony robotic system and the nucleic acids were isolated from the resuspended samples according to the QIAsymphony script.

The first batch was directly processed after resuspension, the second batch after 2 hours 5 minutes. Thus, the samples of the second batch had a 2 hours 5 minutes longer holding time.

Modified Version Comprising the Addition of a Chaotropic Agent During Resuspension The QIAsymphony PAXgene Blood RNA protocol was modified by adding a chaotropic agent to the resuspended sample in order to preserve the RNA integrity. The blood samples were manually prepared as described above. After the resuspension buffer BR1 was added to the pellet and vortexed, 200 µl of a further solution (BR2, QIAGEN) was added which comprises a chaotropic salt (GITC). The chaotropic salt was added to preserve the RNA integrity. The samples were then processed according to two different versions. According to version 1, the samples were directly loaded on the QIAsymphony robot after the buffer BR2 was added. According to version 2, the samples were vortexed after the addition of the buffer BR2 and then loaded on the QIAsymphony robot. In the QIAsymphony robotic system, the nucleic acids were then isolated from the resuspended samples according to the QIAsymphony script.

The quality of the isolated RNA was determined with the Agilent Bioanalyzer and expressed in RIN values (RIN=RNA integrity number).

Results

The results are shown in FIG. 1:
1: QIAsymphony PAXgene Blood RNA—first batch
2: QIAsymphony PAXgene Blood RNA—second batch
3: QIAsymphony PAXgene Blood RNA modified (addition of chaotropic agent)—second batch (no vortexing)
4: QIAsymphony PAXgene Blood RNA modified (addition of chaotropic agent)—second batch (vortexing)

FIG. 1 shows that the RNA integrity is excellent with the first batch of the samples that were processed according to the prior art protocol. However, the RNA integrity decreases in the second batch which had a longer holding time between resuspension of the sample and nucleic acid extraction. Thus, longer holding times decrease the RNA integrity and hence the quality of the RNA.

The modified versions, wherein a chaotropic salt is added to the resuspended samples show no differences with respect to the RNA quality between batch 1 and batch 2. Thus, the RNA integrity is preserved even if the samples have a long holding time of two hours and more.

Example 2

In Example 2, the QIAsymphony PAXgene Blood RNA protocol described above and a modified version (wherein a chaotropic agent is added during resuspension) was analysed with respect to the nucleic acid yield. In said modified version 3 that was tested in Example 2, the nucleic acid isolation was also performed on the QIAsymphony according to the QIAsymphony PAXgene Blood RNA protocol, however, using a modified binding buffer in order to improve nucleic acid binding, in particular the binding of small RNA. The modified binding buffer that was used in Example 2 instead of the binding buffer QSB1 that is used in the QIAsymphony PAXgene Blood RNA protocol, comprised more than 60% isopropanol and 0.2M sodium trichloroacetate. Respectively modified binding buffers to achieve improved binding in particular of small nucleic acids and corresponding nucleic acid isolation protocols are described in EP 10 000 432.4, herein incorporated by reference. The resuspension of the sample was performed as described in Example 1 (modified version) and hence, a chaotropic agent (GITC) was added in form of buffer BR2 to preserve the RNA integrity.

Figure 2:
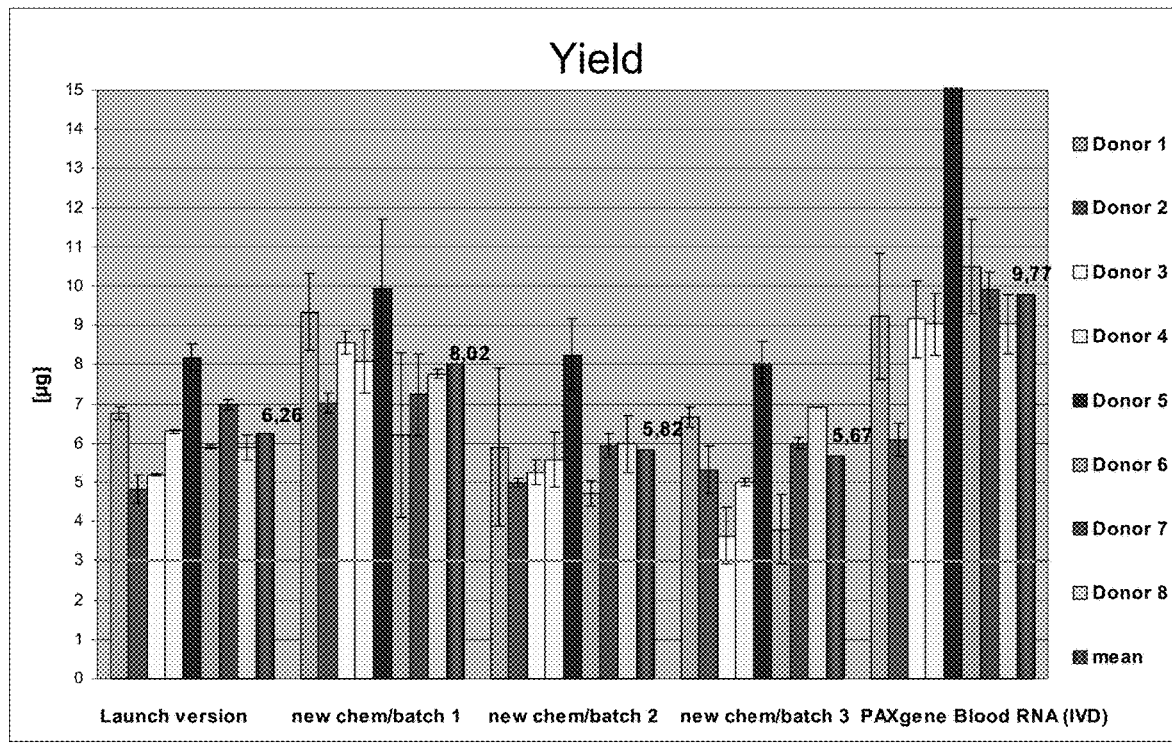
FIG. 2 is a graph showing yield of nucleic acids isolated from blood samples as described in Example 2.

For the respectively modified version 3, 3 batches were tested. The first batch of samples was directly processed after sample resuspension, the second batch had a holding time of 2 hours 5 minutes, the third batch had a holding time of 4 hours 10 minutes. As additional reference, samples were also processed with the PAXgene Blood RNA Kit (a membrane based, single spin column method) according to the manufacturers instructions. The results of Example 2 are shown in FIG. 2:
1: QIAsymphony PAXgene Blood RNA
2: QIAsymphony PAXgene Blood RNA modified (addition of chaotropic agent)—first batch
3: QIAsymphony PAXgene Blood RNA modified (addition of chaotropic agent)—second batch
4: QIAsymphony PAXgene Blood RNA modified (addition of chaotropic agent)—third batch
5: PAXgene Blood RNA (IVD)

As can be derived from FIG. 2, the first batch of the modified version achieves good yields which are also improved compared to the prior art method. However, reduced yields are observed for the $2^{nd}$ and $3^{rd}$ batch with the modified version, wherein the chaotropic agent is added to the resuspended sample to guarantee high RIN values (see Example 1 and FIG. 1). The yield is reduced up to 20 to 30%. The reason for this loss in nucleic acid yield is that a precipitate is formed during the holding time which sticks tightly to the plastic wall of the tube.

Example 3

In order to ensure both, a high RNA integrity and a high nucleic acid yield, the protocol was modified according to the teachings of the present invention. Thus, the pellet was resuspended by adding a modified resuspension buffer, which additionally comprised EDTA. For this purpose, 25 mM EDTA was added to the resuspension buffer BR1 (QIAGEN) that is used for resuspension in the prior art protocol. 280 µl of this modified resuspension buffer BR1 was added to the pellet that was obtained from the PAXgene stabilised blood samples (see Example 1). Furthermore, for resuspension 20 µl proteinase K was added per sample. The sample was resuspended by vortexing and 200 µl of a buffer comprising a chaotropic agent (BR2, QIAGEN—comprises >3M GITC) was added.

The resuspended samples were loaded on the QIAsymphony robotic system and the automated nucleic acid extraction was performed. In brief, the nucleic acid isolation protocol comprised the following steps:
1. Sample Digestion
    40 µl proteinase K was added to the resuspended sample and incubated for 10 min under heating and shaking.
2. DNA Removal
    Mag Attract G beads (QIAGEN) were added to the digested sample to bind the DNA to the beads. The beads were than removed from the sample.
3. RNA Binding
    Mag Attract G beads (QIAGEN) were added and 1500 µl of a binding buffer comprising more than 65% isopropanol, sodium trichloroacetate and a Tris buffer.
4. Washing
    Two washing steps were performed using the washing buffers QSB1 and BR4 (QIAGEN).
5. DNase and Proteinase K Digest
    The RNA was eluted and DNA traces were digested using DNase I. Afterwards, a second proteinase K digest was performed (see EP 10 007 346.9, herein incorporated by reference).
6. RNA Re-Binding
    1400 µl of the binding buffer (see above) was added.
7. Washing
    4 final washing steps were performed (using the buffers QSB1, QSW5 and BR4, all QIAGEN).
8. Elution and Heat Denaturation
    The RNA was eluted using 200 µl BR5 (QIAGEN) and the eluted nucleic acid was heat denatured for 10 min.

24 blood samples were collected per batch in PAXgene Blood RNA Tubes. This protocol according to the present invention was compared to the modified version as described in example 2 (wherein a chaotropic agent was added during resuspension to preserve the RNA integrity but no EDTA). Three batches were tested in each method. The first batch was directly processed after sample resuspension, the second batch had a holding time of 2 hours 20 minutes hours, the third batch had a holding time of 4 hours 40 minutes hours. As additional reference, samples were processed with the PAXgene Blood RNA kit (membrane based, single spin column method).

The results are shown in FIGS. 3 to 6.

Figure 3:
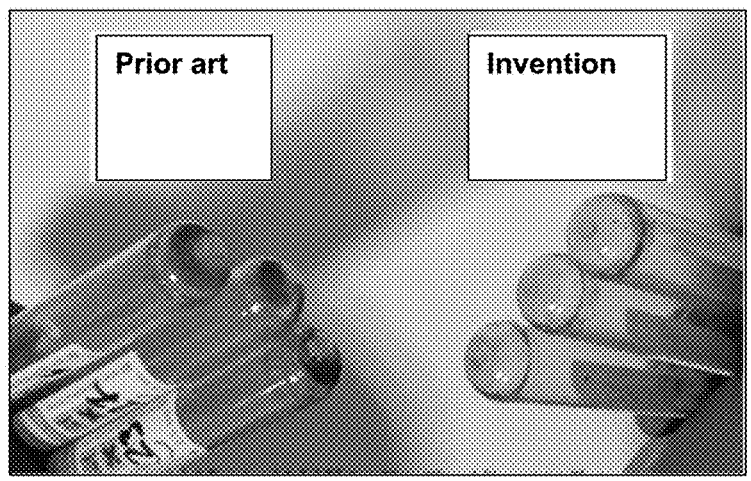
FIG. 3 shows the effects of resuspension steps on precipitate formation at the bottom of test tubes as described in Example 3.

FIG. 3 shows the effect of the modified resuspension step according to the present invention on the precipitate formation. On the left hand side, the tubes of the $3^{rd}$ batch are shown wherein the samples were prepared according to the modified version (see example 2), wherein a chaotropic agent is added during resuspension (but no EDTA). As can be seen, a large precipitate is formed which irreversibly sticks to the container walls and thus, is lost for the subsequent nucleic acid isolation (=reduced yield, see example 2). On the right hand side, the tubes of the $3^{rd}$ batch are shown wherein the samples were prepared according to the method of the present invention, wherein EDTA is added during resuspension in addition to the chaotropic agent. As can be seen, the precipitate formation is substantially prevented with the method according to the present invention.

Figure 4:
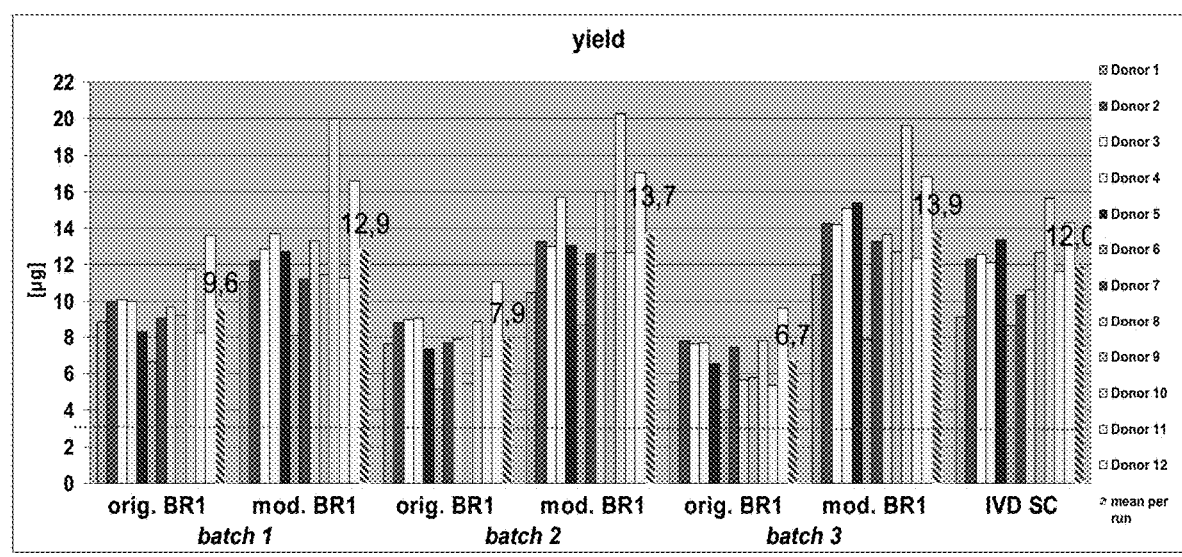
FIG. 4 is a graph showing yields of nucleic acids isolated from blood samples as described in Example 3.

FIG. 4 shows the overall RNA yield that is obtained with different batches of the protocols under comparison:
1: QIAsymphony PAXgene Blood RNA—first batch
2: QIAsymphony PAXgene Blood RNA modified according to the invention—first batch
3: QIAsymphony PAXgene Blood RNA—second batch
4: QIAsymphony PAXgene Blood RNA modified according to the invention—second batch
5: QIAsymphony PAXgene Blood RNA—third batch
6: QIAsymphony PAXgene Blood RNA modified according to the invention—third batch
7: PAXgene Blood RNA (IVD)

FIG. 4 demonstrates that the samples that are processed according to the method of the present invention achieve constant high nucleic acid yields despite longer holding times between the different batches. The nucleic acid yield is considerably improved.

Figure 5:
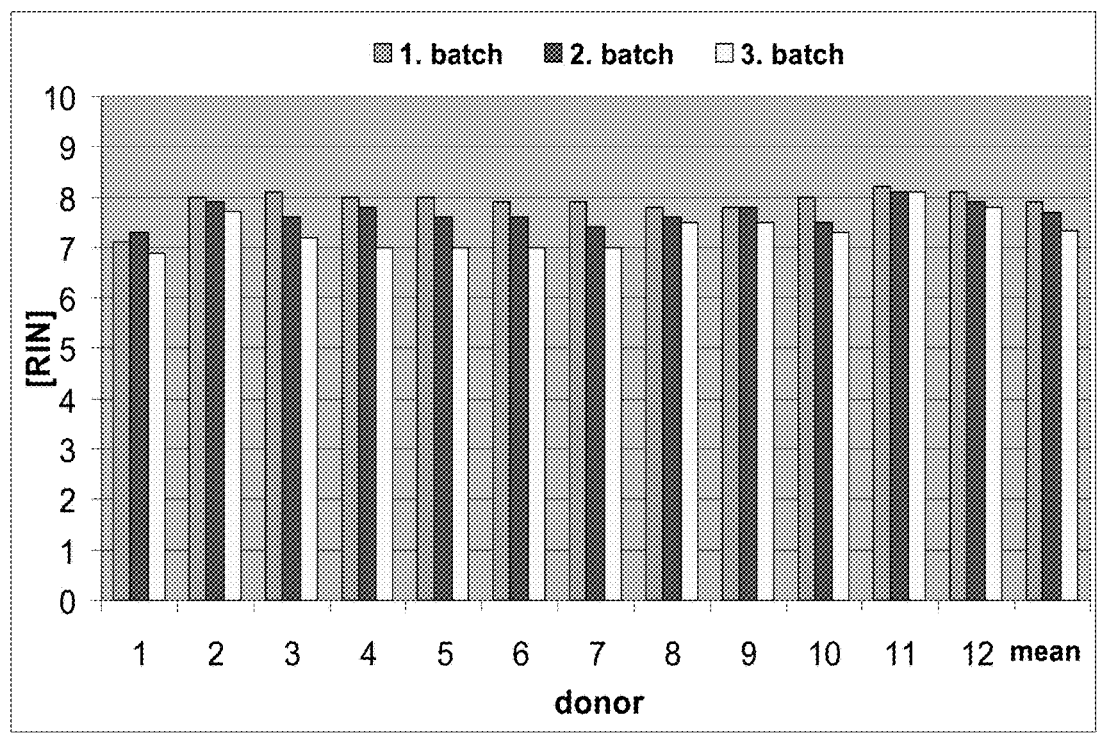
FIG. 5 is a graph showing RIN values of RNA isolated as described in Example 3.

FIG. 5 shows the RNA integrity that is achieved with the method according to the present invention. As can be seen, a high RIN is obtained with all three batches. Thus, the integrity of the RNA is preserved, despite long holding times.

Figure 6:
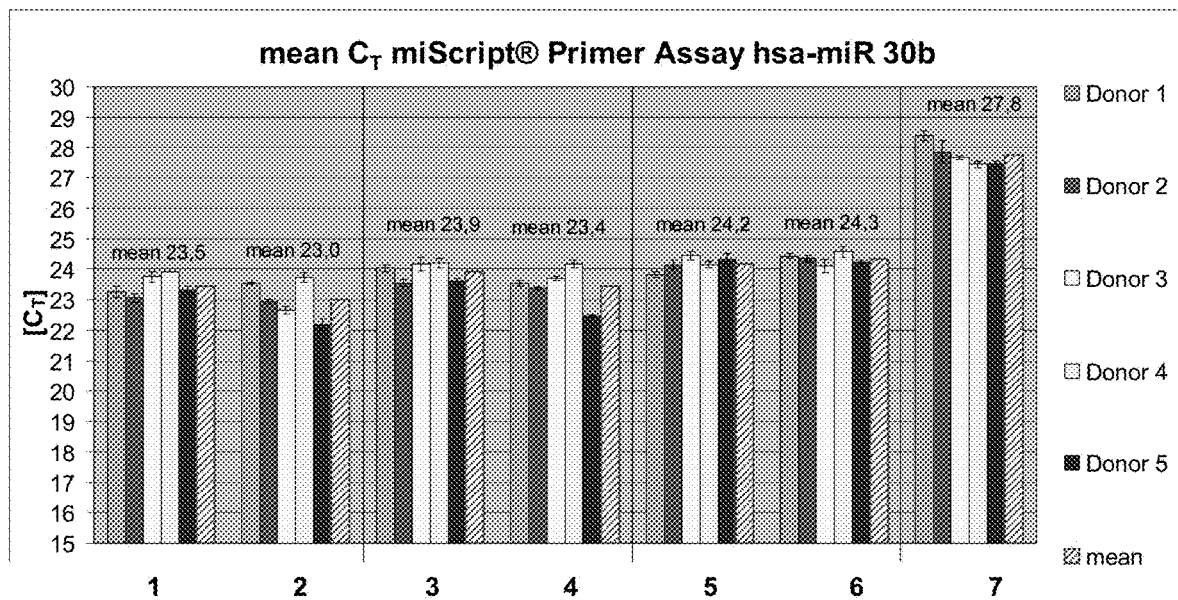
FIG. 6 is a graph showing $C_T$ values obtained with the MISCRIPT® primer assay (hsa-miR30b) when analyzing eluates obtained as described in Example 3.

FIG. 6 demonstrates the achieved yield of small RNAs:
1: QIAsymphony PAXgene Blood RNA—first batch
2: QIAsymphony PAXgene Blood RNA modified according to the invention—first batch
3: QIAsymphony PAXgene Blood RNA—second batch
4: QIAsymphony PAXgene Blood RNA modified according to the invention—second batch
5: QIAsymphony PAXgene Blood RNA—third batch
6: QIAsymphony PAXgene Blood RNA modified according to the invention—third batch
7: PAXgene Blood RNA (IVD)

FIG. 6 shows the mean $C_T$ obtained with the miScript® Primer assay (hsa-miR 30b) when analysing the eluates obtained with the different tested protocols. As can be seen, the method achieves a good yield of small RNAs which is also considerably improved compared to the prior art method.

Example 4

In example 4, the effects of the addition of EDTA during resuspension on the RNA yield was further analysed. Optionally, a protein-degrading compound (proteinase K) was added. For each test series, 24 test tubes (PAXgene Blood RNA Tubes from QIAGEN) filled with 2.5 ml whole human blood were obtained in duplicates from 12 individual donors and the nucleic acid containing pellet was obtained. The supernatants were removed, and the pellets were resuspended by vortexing in the fresuspension buffer BR1 (QIAGEN):

- 280 µl BR1 (QIAGEN), 20 µl proteinase K solution (QIAGEN) and 200 µl of a GITC containing buffer (BR2, QIAGEN);
- 280 µl BR1 (QIAGEN)+10 mM EDTA, 20 µl proteinase K solution (QIAGEN) and 200 µl of a GITC containing buffer (BR2, QIAGEN);
- 280 µl BR1 (QIAGEN)+25 mM EDTA, 20 µl proteinase K solution (QIAGEN) and 200 µl of a GITC containing buffer (BR2, QIAGEN);
- 280 µl BR1 (QIAGEN)+50 mM EDTA, 20 µl proteinase K solution (QIAGEN) and 200 µl of a GITC containing buffer (BR2, QIAGEN);
- 280 µl BR1 (QIAGEN)+25 mM EDTA, 20 µl proteinase K solution (QIAGEN) and 200 µl of a GITC containing buffer (BR2, QIAGEN); or 300 µl BR1 (QIAGEN)+25 mM (no proteinase K) and 200 µl of a GITC containing buffer (BR2, QIAGEN).

The samples were processed according to the protocol described in Example 3.

Figure 7:
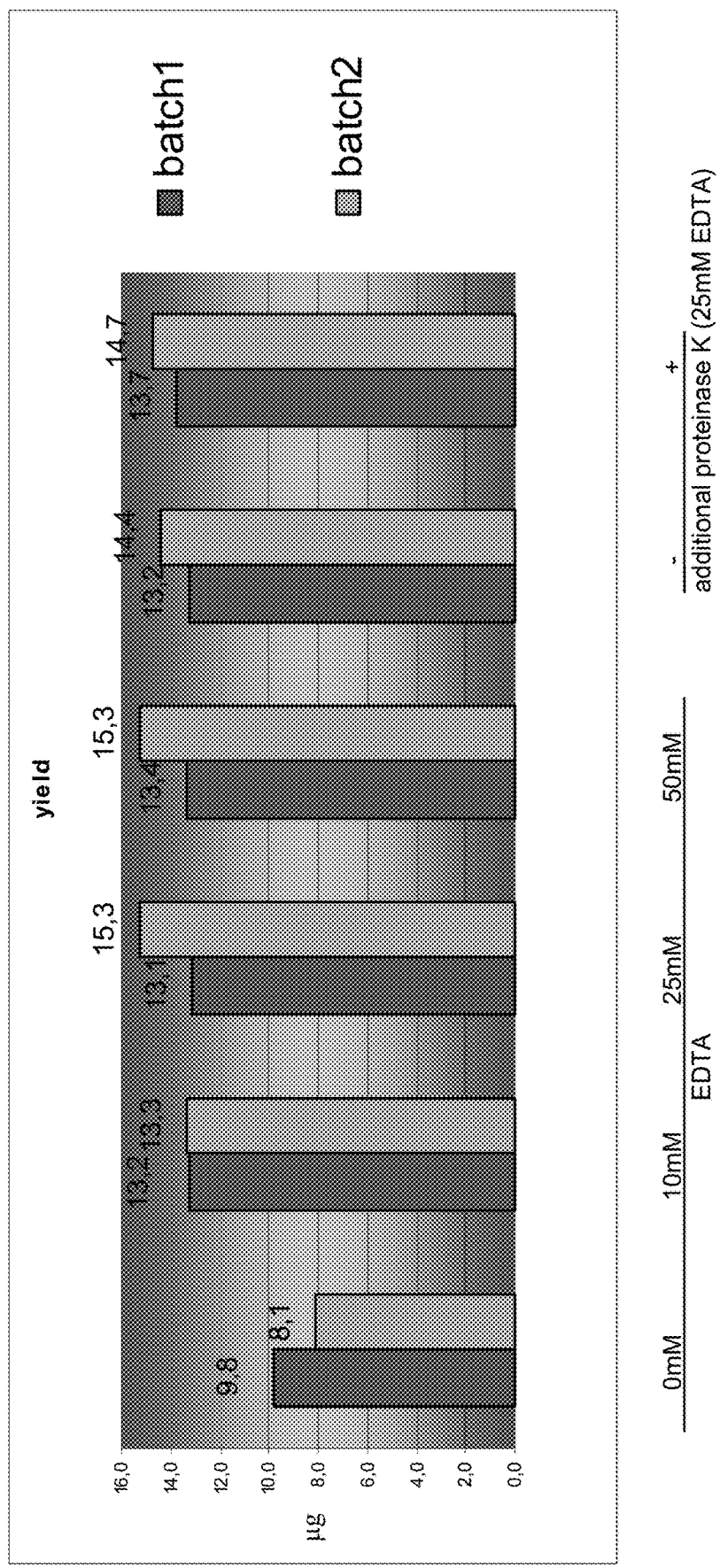
FIG. 7 shows the mean yield of total RNA isolated according to Example 4.

FIG. 7 shows the mean total RNA yield. For samples resuspended in buffer BR1 with proteinase K and the chaotropic agent but no EDTA, the RNA yield achieved from batch 1 samples (with short holding time) was higher than for batch 2 samples (with extended holding time). Samples that were resuspended using a chaotropic agent, proteinase K and the chelating agent EDTA generally yielded more RNA as can be seen from the nucleic acid yields that are obtained with the first batch. Thus, the RNA yield was generally improved. Furthermore, the RNA yield that is obtained from the second batch of samples after an extended holding time is comparable or—at higher EDTA concentrations (25 mM and 50 mM)—even better than the RNA yield that is obtained with the first batch. Similar results are achieved if the proteinase K is omitted during resuspension. Thus, the beneficial effect on the RNA yield is attributable to the addition of the chelating agent.

Example 5

As explained above, the resuspended samples form precipitates during longer holding times, in particular if a chaotropic agent is added during resuspension. Precipitated aggregates remain stuck to the test tube after RNA-processing and are therefore not included in the purification procedure. As a consequence, blood samples of later batches show more pronounced precipitation than samples from earlier batches. Example 5 shows that the precipitate formation and adherence to the container wall that reduces the RNA yield (see above) occurs irrespective of the container material and thus in glass tubes as well as in plastic tubes.

Samples of stabilized whole human blood (using the PAXgene stabilisation chemistry) were processed in glass or plastic tubes. The stabilized samples were centrifuged, the supernatants were removed, and the pellets were resuspended by vortexing in a mixture of 300 µl buffer BR1 and 200 µl buffer BR2. Furthermore, the resuspension protocol according to the present invention was tested, wherein additionally 25 mM EDTA was added during resuspension.

The resuspended samples were left aside for 4 hours. Then, the supernatants were removed and the precipitates were documented in both glass- and plastic-test tubes.

Figure 8A:
FIG. 8A shows bulk precipitates stuck at the bottom of test tubes for samples resuspended without EDTA as described in Example 5.
Figure 8B:
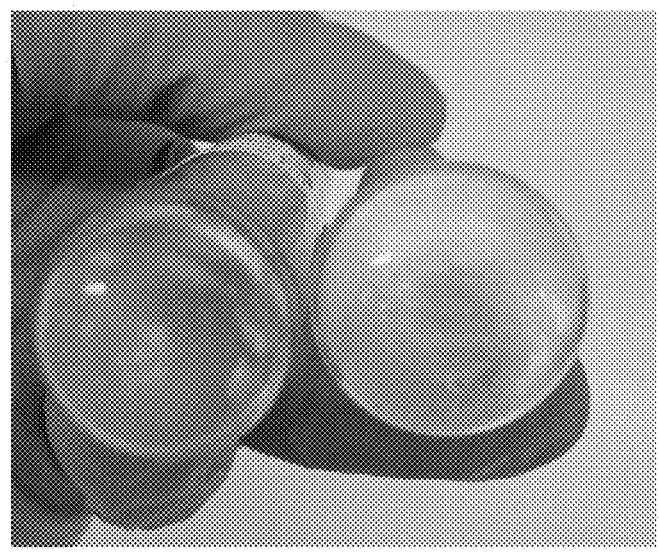
FIG. 8B shows no precipitates at the bottom of test tubes for samples resuspended with EDTA as described in Example 5.

The results are shown in FIG. 8A and FIG. 8B. For both materials tested, bulk precipitates were found stuck at the test tube bottom for the samples that were resuspended without EDTA (see FIG. 8A), representing lost material that will not be included in the subsequent RNA isolation procedure and thus results in reduced nucleic acid yields. Samples that were resuspended according to the method according to the present invention, wherein accordingly, EDTA was additionally included during resuspension, no precipitates were found even after a holding time of 4 hours.

The invention claimed is:

1. A method for isolating nucleic acids from a sample, comprising:
   a) obtaining a sample which has been stabilised by the use of at least one cationic detergent, wherein the cationic detergent has formed complexes with the nucleic acids;
   b) obtaining the complexes optionally together with other sample components from the stabilised sample, wherein said complexes comprise the nucleic acids to be isolated;
   c) generating a resuspended sample comprising
      i) the nucleic acid to be isolated;
      ii) at least one chaotropic agent;
      iii) at least one chelating agent; and
      iv) at least one non-chaotropic salt,
   and
   d) isolating nucleic acids from the resuspended sample, wherein the isolated nucleic acids comprise RNA.

2. The method according to claim 1, wherein the resuspended sample is put on hold between step c) and step d) for at least 0.2 h, at least 0.3 h, at least 0.4 h, at least 0.5 h, at least 0.75 h or at least 1 h and/or for a time period of 0.5 h to 12 h, 1 h to 10 h, 1.5 h to 8 h, 2 h to 7 h or 3 h to 6 h.

3. The method according to claim 1, wherein the resuspension performed in step c) has one or more of the following characteristics:
   a) a resuspension solution is added wherein said resuspension solution comprises the non-chaotropic salt;
   b) the chelating agent is added before, during or after resuspension;
   c) the chelating agent is added separately from the resuspension solution;
   d) the chelating agent is comprised in a resuspension solution;
   e) the chelating agent is added in a concentration so that the resuspended sample comprises the chelating agent in a concentration selected from 0.5 mM to 75 mM, 1 mM to 50 mM, 2.5 mM to 25 mM and 5 to 15 mM;
   f) the chelating agent is selected from the group consisting of diethylenetriaminepentaacetic acid (DTPA), ethylenedinitrilotetraacetic acid (EDTA), ethylene glycol tetraacetic acid (EGTA) and N,N-bis(carboxymethyl) glycine (NTA) and/or
   g) at least one additive is added before, during and/or after resuspension which is selected from the group consisting of chaotropic agents, protein-degrading compounds and buffering agents, and thereby is comprised in the resuspended sample.

4. The method according to claim 3, wherein the resuspension performed in step c) has characteristic a), and wherein the non-chaotropic salt of characteristic a) is an ammonium salt.

5. The method according to claim 1, wherein the chelating agent present in the resuspended sample
   a) reduces binding of the precipitated sample to the container comprising the sample;
   b) increases the yield of the isolated nucleic acid; and/or
   c) reduces variations in the nucleic acid isolation efficiency or quantity attributable to different holding times between step c) and d).

6. The method according to claim 1, wherein said method has with respect to the chaotropic agent comprised in the resuspended sample one or more of the following characteristics:
   a) the concentration of the chaotropic agent in the resuspended sample is selected from the group consisting of 0.1 M to 4 M, 0.5M to 3M and 0.75M to 2.5M;
   b) the concentration of the chaotropic agent in the resuspended sample is at least 1M;
   c) the chaotropic agent is added in step c) in form of a separate solution;
   d) the chaotropic agent is added in step c) after resuspension of the complexes and thereby is comprised in the resuspended sample;
   e) the chaotropic agent present in step c) is selected from the group consisting of chaotropic salts, guanidinium hydrochloride, guanidinium thiocyanate (GTC), guanidinium isothiocyanate (GITC), sodium thiocyanate, sodium iodide, sodium perchlorate, sodium trichloroacetate, sodium trifluroacetate and urea; and/or
   f) the chaotropic agent present in step c) is selected from GTC and GITC.

7. The method according to claim 1, wherein step d) comprises binding the nucleic acids to a solid phase comprising silica.

8. The method according to claim 1, wherein a protein degrading compound is added in step c).

9. The method according to claim 8, wherein the protein degrading compound is a proteolytic enzyme optionally selected from the group consisting of proteinases, proteases, subtilisins and subtilases.

10. The method according to claim 9, wherein the proteolytic enzyme is added before or during resuspension of the complexes.

11. The method according to claim 10, wherein the proteolytic enzyme is proteinase K.

12. The method according to claim 1, wherein step c) comprises:
    aa) adding a resuspension solution that comprises a non-chaotropic salt and a chelating agent but no chaotropic agent, thereby resuspending the complexes,
    bb) adding a chaotropic agent after resuspension of the complexes so that the chaotropic agent is comprised in the resuspended sample, and
    cc) optionally adding a proteolytic enzyme before, during or after resuspension of the complexes and thereby is included in the resuspended sample.

13. The method according to claim 12, wherein in step bb), the chaotropic agent is added to the resuspended complexes in form of an aqueous solution.

14. The method according to claim 1, wherein the isolation performed in step d) comprises the following steps:
    i) digesting and/or denaturing the resuspended sample, optionally by heating and/or agitating the resuspended sample in the presence of a proteolytic enzyme;
    ii) binding the nucleic acids to a solid phase using appropriate binding conditions, and
    iii) optionally washing the nucleic acids;
    iv) optionally eluting the nucleic acids.

15. The method according to claim 1, wherein the sample is a blood sample and in step a), the blood sample is stabilised by contacting the blood sample with a stabilizing composition comprising:
   i) a cationic compound of the general formula:

$Y^+R_1R_2R_3R_4X^-$ wherein Y represents nitrogen or phosphor,
   $R_1R_2R_3$ and $R_4$ independently, represent a branched or unbranched $C_1$-$C_{20}$-alkyl group, a $C_6$-$C_{20}$-aryl group and/or a $C_6$-$C_{26}$ aralkyl group; and
   $X^-$ represents an anion of an inorganic or organic, mono- or polybasic acid; and
   ii) at least one proton donor.

16. The method according to claim 1, wherein the sample is a blood sample, and in step a), the blood sample is stabilised by contacting the blood sample with a stabilizing composition comprising:
   (i) an amino surfactant having the following formula (2):

R1R2R3N(O)x    (2)

wherein
   R1 and R2 each independently is H, C1-C6 alkyl residue, C6-C12 aryl residue or C6-C12 aralkyl residue,
   R3 is C1-C20 alkyl group, C6-C26 aryl residue, or C6-C26 aralkyl residue,
   X is an integer of 0 and 1, and
   (ii) an acid or acid salt.

17. The method according to claim 2, wherein a plurality of samples is processed and wherein the holding time between step c) and step d) differs at least between some of the resuspended samples.

18. The method according to claim 1, having one or more of the following characteristics:
   a) a plurality of samples is prepared according to steps a) to c) thereby providing a plurality of resuspended samples, wherein the resuspended samples are divided into batches, and the nucleic acids are isolated from the batches according to step d), and wherein the holding time between step c) and d) varies at least between two batches;
   b) step d) is performed using an automated system;
   c) a plurality of samples is processed manually up to step c) thereby providing a plurality of resuspended samples, and wherein the resuspended samples are processed using an automated system for isolating the nucleic acids in step d); and/or
   d) at least RNA is isolated from a sample comprising at least RNA and DNA and wherein isolation step d) comprises
      obtaining the resuspended sample comprising a proteolytic enzyme and continuing the digestion of the resuspended sample;
      removing at least a portion of the DNA from the resuspended and digested sample by binding DNA to a first solid phase and separating the DNA bound to said first solid phase from the remaining sample comprising the RNA,
      binding the RNA to a second solid phase, wherein at least one chaotropic agent and at least one alcohol in a concentration ≥30% v/v is used during this RNA binding step,
      optionally performing at least one washing step for washing the RNA bound to said second solid phase,
      optionally performing a DNase digest and/or a digest using a proteolytic enzyme, and
      optionally eluting the RNA.

19. The method according to claim 18, wherein the method has characteristic d), and in characteristic d), digestion of the sample is performed by incubating the resuspended sample for at least 5 min above room temperature or above 50° C.

20. The method according to claim 1, wherein the method is for isolating RNA from a blood sample, comprising the following steps:
   a) obtaining a sample which has been stabilised by the use of at least one cationic detergent, wherein the cationic detergent has formed complexes with the nucleic acids;
   b) obtaining the complexes optionally together with other sample components from the stabilised sample, wherein said complexes comprise the nucleic acids to be isolated;
   c) resuspending the complexes and optionally adding one or more additives before, during and/or after resuspension, wherein step c) comprises
      aa) adding a resuspension solution which comprises a non-chaotropic salt and a chelating agent wherein the resuspension solution does not comprise a chaotropic salt and resuspending the complexes,
      bb) adding a chaotropic agent after resuspension of the complexes wherein optionally, the chaotropic agent is added to the resuspended complexes in form of an aqueous solution, and
      cc) optionally adding a proteolytic enzyme before, during or after resuspension of the complexes, thereby obtaining a resuspended sample comprising at least
         i) the nucleic acid to be isolated;
         ii) at least one chaotropic agent; and
         iii) at least one chelating agent; and
         iv) optionally a proteolytic enzyme;
   and
   d) isolating RNA from the resuspended sample;
      wherein a plurality of samples is prepared according to steps a) to c) thereby providing a plurality of resuspended samples, wherein the resuspended samples are divided into batches and the nucleic acids are isolated from the batches according to step d) and wherein the holding time between step c) and d) varies at least between two batches.

21. The method according to claim 20, wherein the isolation of RNA in step d) comprises:
   at least RNA is isolated from a sample comprising at least RNA and DNA and wherein isolation step d) comprises
      obtaining the resuspended sample comprising a proteolytic enzyme and continuing the digestion of the resuspended sample;
      removing at least a portion of the DNA from the resuspended and digested sample by binding DNA to a first solid phase and separating the DNA bound to said first solid phase from the remaining sample comprising the RNA,
      binding the RNA to a second solid phase, wherein at least one chaotropic agent and at least one alcohol in a concentration ≥30% v/v is used during this RNA binding step,
      optionally performing at least one washing step for washing the RNA bound to said second solid phase,
      optionally performing a DNase digest and/or a digest using a proteolytic enzyme, and
      optionally eluting the RNA.

22. The method according to claim 1, wherein step d) is performed using an automated system using magnetic particles.

23. The method of claim 4, wherein the ammonium salt is ammonium acetate or ammonium sulphate.

24. The method according to claim 3, wherein the resuspension performed in step c) has characteristic a), and wherein the non-chaotropic salt of characteristic a) is an alkali metal salt.

25. The method of claim 24, wherein the alkali metal salt is KCl or NaCl.

26. The method of claim 12, wherein the chaotropic agent is a chaotropic salt selected from the group consisting of guanidinium thiocyanate, guanidinium isothiocyanate, sodium thiocyanate, sodium iodide, sodium perchlorate, sodium trichloroacetate, and sodium trifluroacetate.

27. The method of claim 26, wherein the chaotropic agent is guanidinium thiocyanate or guanidinium isothiocyanate.

28. The method of claim 12, wherein the chelating agent is selected from the group consisting of diethylenetriaminepentaacetic acid (DTPA), ethylenedinitrilotetraacetic acid (EDTA), ethylene glycol tetraacetic acid (EGTA), and N,N-bis(carboxymethyl)glycine (NTA).

29. The method of claim 12, wherein the chelating agent is ethylenedinitrilotetraacetic acid (EDTA).

30. The method according to claim 1,
wherein step c) comprises
aa) adding a resuspension solution that comprises a non-chaotropic salt and a chelating agent, but does not comprise a chaotropic agent, and resuspending the complexes,
    wherein the non-chaotropic salt is an ammonium salt, and wherein the chelating agent is selected from the group consisting of diethylenetriaminepentaacetic acid (DTPA), ethylenedinitrilotetraacetic acid (EDTA), ethylene glycol tetraacetic acid (EGTA), and N,N-bis(carboxymethyl)glycine (NTA),
bb) adding a chaotropic agent after respension of the complexes whereby the chaotropic agent becomes comprised in the resuspended sample,
    wherein the chaotropic agent is a chaotropic salt selected from the group consisting of guanidinium thiocyanate, guanidinium isothiocyanate, sodium thiocyanate, sodium iodide, sodium perchlorate, sodium trichloroacetate and sodium trifluroacetate, and
wherein step d) is performed using an automated system.

31. The method of claim 30, wherein magnetic particles are used for nucleic acid binding in step d).

32. The method of claim 1, wherein the chelating agent is added prior to the addition of the chaotropic agent.

* * * * *